(12) United States Patent
Davies

(10) Patent No.: US 10,653,140 B2
(45) Date of Patent: May 19, 2020

(54) INDUCTION OF A PHYSIOLOGICAL DISPERSION RESPONSE IN BACTERIAL CELLS IN A BIOFILM

(71) Applicant: The Research Foundation for The State University of New York, Binghamton, NY (US)

(72) Inventor: David G. Davies, Binghamton, NY (US)

(73) Assignee: The Research Foundation for The State University of New York, Binghamton, NY (US)

(*) Notice: Subject to any disclaimer, the term of this patent is extended or adjusted under 35 U.S.C. 154(b) by 390 days.

(21) Appl. No.: 13/945,207

(22) Filed: Jul. 18, 2013

(65) Prior Publication Data

US 2013/0302390 A1 Nov. 14, 2013

Related U.S. Application Data

(62) Division of application No. 12/152,347, filed on May 14, 2008, now Pat. No. 8,513,305.

(60) Provisional application No. 60/917,791, filed on May 14, 2007, provisional application No. 61/018,639, filed on Jan. 2, 2008.

(51) Int. Cl.
| | | |
|---|---|---|
| *A01N 37/06* | (2006.01) | |
| *A61Q 11/00* | (2006.01) | |
| *A01N 37/02* | (2006.01) | |
| *A61K 8/36* | (2006.01) | |
| *A01N 37/18* | (2006.01) | |
| *A61K 8/49* | (2006.01) | |
| *G02B 1/04* | (2006.01) | |

(52) U.S. Cl.
CPC ............. *A01N 37/06* (2013.01); *A01N 37/02* (2013.01); *A01N 37/18* (2013.01); *A61K 8/361* (2013.01); *A61K 8/4973* (2013.01); *A61Q 11/00* (2013.01); *G02B 1/043* (2013.01)

(58) Field of Classification Search
CPC .................................................. A61Q 11/00
See application file for complete search history.

(56) References Cited

U.S. PATENT DOCUMENTS

| | | | |
|---|---|---|---|
| 4,097,604 A | 6/1978 | Thiele | |
| 4,214,006 A | 7/1980 | Thiele | |
| 4,215,144 A | 7/1980 | Thiele | |
| 4,224,307 A | 9/1980 | Thiele et al. | |
| 4,442,125 A | 4/1984 | Thiele | |
| 5,428,101 A | 6/1995 | Urano et al. | |
| 5,798,117 A | 8/1998 | New et al. | |
| 6,455,031 B1 | 9/2002 | Davies et al. | |
| 6,830,745 B1 | 12/2004 | Budny et al. | |
| 6,936,447 B1 | 8/2005 | Pearson et al. | |
| 6,991,810 B1 | 1/2006 | Grundy et al. | |
| 7,018,642 B2 | 3/2006 | Degenhardt et al. | |
| 7,094,394 B2 | 8/2006 | Davies et al. | |
| 2002/0123077 A1 | 9/2002 | O'Toole et al. | |
| 2003/0035779 A1* | 2/2003 | Brown et al. | 424/49 |
| 2004/0097402 A1* | 5/2004 | Bassler et al. | 514/2 |
| 2004/0235914 A1 | 11/2004 | Ammendola et al. | |
| 2004/0241107 A1* | 12/2004 | Burzynski | A61K 8/23 |
| | | | 424/49 |
| 2005/0084545 A1 | 4/2005 | Pipko et al. | |
| 2006/0165648 A1 | 7/2006 | Degenhardt et al. | |
| 2007/0014739 A1 | 1/2007 | Eldridge et al. | |
| 2007/0207095 A1 | 9/2007 | Davies | |

FOREIGN PATENT DOCUMENTS

| | | |
|---|---|---|
| DE | 2310246 A1 | 9/1974 |
| DE | 2349090 A1 | 4/1975 |
| JP | 54-95535 A | 7/1979 |
| JP | 58-213716 A | 12/1983 |

(Continued)

OTHER PUBLICATIONS

Wang et al, "A Bacterial Cell-Cell Communication Signal with Cross-Kingdom Structural Analogues," Molecular Microbiology, vol. 51, No. 3, pp. 903-912 (2004).*
McDonnell et al, "Antiseptics and Disinfectants: Activity, Action, and Resistance," Clinical Microbiology Reviews, vol. 12, No. 1, pp. 147-179 (1999).*
Thompson et al., "Chemical Reactions Involved in the Deep-fat Frying of Foods. VII. Identification of Volatile Decomposition Products of Trilinolein," Journal of the American Oil Chemists' Society 55:897-901 (1978).
Zhang et al., "Blocking of Candida Albicans Biofilm Formation by Cis-2-Dodecenoic Acid and Trans-2-Dodecenoic Acid," Journal of Medical Microbiology 60:1643-50 (2011).

(Continued)

*Primary Examiner* — Dennis J Parad
(74) *Attorney, Agent, or Firm* — Tully Rinckey PLLC; Steven N. Hoffberg

(57) ABSTRACT

One aspect of the present invention is directed to a composition. The composition includes a dispersion inducer comprising:

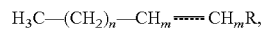

$H_3C-(CH_2)_n-CH_m = CH_mR$, where ═ is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains an additive component selected from one or more of the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm. The present invention is also directed to methods of using this compound.

6 Claims, 18 Drawing Sheets

(56) References Cited

FOREIGN PATENT DOCUMENTS

| | | |
|---|---|---|
| JP | 59-193809 A | 11/1984 |
| JP | 59-199606 A | 11/1984 |
| JP | 60-9728 A | 1/1985 |
| JP | 61-106501 A | 5/1986 |
| JP | 2-241546 A | 9/1990 |
| JP | 7-173166 A | 7/1995 |
| JP | 10-182450 A | 7/1998 |
| JP | 2002-241546 A | 8/2002 |
| JP | 2003-137758 A | 5/2003 |
| JP | 2004-018431 A | 1/2004 |
| JP | 200662966 A | 3/2006 |
| JP | 2007-239280 A | 9/2007 |
| JP | 2007-262050 A | 10/2007 |
| WO | 02/27018 A2 | 4/2002 |
| WO | 2005034933 A1 | 4/2005 |
| WO | 2007081455 | 7/2007 |
| WO | 2007092633 A2 | 8/2007 |

OTHER PUBLICATIONS

Ramage et al., "Inhibition of Candida Albicans Biofilm Formation by Farnesol, a Quorum-Sensing Molecule," Applied and Environmental Microbiology 68(11):5459-63 (2002).
Boon et al., "A Novel DSF-like Signal from Burkholderia cenocepacia Interferes with Candida albicans Morphological Transition," The ISME Journal 2:27-36 (2008).
Davies & Marques, "A Fatty Acid Messenger is Responsible for Inducing Dispersion in Microbial Biofilms," Department of Biological Sciences, State University of New York at Binghamtom.
Davies et al., "Exopolysaccharide Production in Biofilms: Substratum Activation of Alginate Gene Expression by Pseudomonas aeruginosa," Appl. Environ. Microbiol. 59(4):1181-6 (1993).
Davies & Geesey, "Regulation of the Alginate Biosynthesis Gene algC in Pseudomonas aeruginosa During Biofilm Development in Continuous Culture," Appl. Environ. Microbiol. 61(3):860-7 (1995).
Davies et al., "The Involvement of Cell-to-Cell Signals in the Development of a Bacterial Biofilm," Science 280(5361):295-8 (1998).
Rashid et al., "Polyphosphate Kinase is Essential for Biofilm Development, Quorum Sensing, and Virulence of Pseudomonas aeruginosa," Proc Nat'l Acad Sci 97(17):9636-41 (2000).
Sauer et al., "Pseudomonas aeruginosa Displays Multiple Phenotypes During Development as a Biofilm," Journal of Bacteriology 184(4):1140-54 (2002).
Stoodley et al., "Biofilms as Complex Differentiated Communities," Annual Review of Microbiology 56:187-209 (2002).
International Search Report for International Patent Application No. PCT/US08/06171 (dated Aug. 22, 2008).
Dow et al., "Biofilm Dispersal in Xanthomonas campestris is Controlled by Cell-Cell Signaling and is Required for Full Virulence to Plants," PNAS 100(19):10995-11000 (2003).
Wang et al., "A Bacterial Cell-Cell Communication Signal with Cross-Kingdom Structural Analogues," Molecular Microbiology 51(3):903-912 (2004).
Ryan et al., "Diffusible Signals and Interspecies Communication in Bacteria," Microbiology 154:1845-1858 (2008).
Marques et al., "Induction of Biofilm Dispersion in Multiple Bacterial Species in Response to a Common Inducer," American Society for Microbiology (abstract).
Smith et al., "Induction and Inhibition of Pseudomonas aeruginosa Quorum Sensing by Synthetic Autoinducer Analogs," Chemistry & Biology 10:81-89 (2003).
Erickson et al., "Pseudomonas aeruginoas Quorum-sensing Systems May Control Virulence Factor Expression in the Lungs of Patients with Cystic Fibrosis," Infection and Immunity 70(4):1783-1790 (2002).
International Search Report dated Nov. 20, 2007.
Rice et al., "Biofilm Formation and Sloughing in Serratia marcescens are Controlled by Quorum Sensing and Nutrient Cues," J. Bacteriol. 187(10):3477-3485 (2005).
Mireles et al., "*Salmonella enterica* Serovar Typhimurium Swarning Mutants with Altered Biofilm-Forming Abilities: Surfactin Inhibits Biofilm Formation," J. Bacteriol. 183(20):5848-5854 (2001).
Irie et al., "Pseudomonas aeruginosa Rhamnolipids Disperse Bordetella bronchiseptica Biofilms," FEMS Microbiol. Ltrs. 250:237-243 (2005).
Borchardt et al., "Reaction of Acylated Homoserine Lactone Bacterial Signaling Molecules with Oxidized Halogen Antimicrobials," Appl. Environ. Microbiol. 67(7):3174-3179 (2001).
Davies et al., Abstract Q-161, "Autodispersion in Pseudomonas Aeruginosa Biofilms," ASM 103rd General Meeting, Washington, D.C. (May 20, 2003), Biosciences Information Service, XP009133214, Database Accession No. PREV200300546547 (Abstract).
Davies et al., Abstract Q-100, "Autoinduction of Pseudomonas Aeruginosa Biofilm Dispersion," ASM 105th General Meeting, Atlanta, GA (Jun. 6, 2005), Biosciences Information Service, XP009133221, Database Accession No. PREV200800237844 (Abstract).
Tagliente et al., Abstract Q-20, "Development and Dispersion of Pseudomonas Aeruginosa Biofilms," ASM 101st General Meeting, Orlando, Florida (May 21, 2001), Biosciences Information Service, XP009133213, Database Accession No. PREV200200233614 (Abstract).
Extended European Search Report for European Patent Application No. EP06849263 (dated Jun. 10, 2010).
Monteiro et al., "Molecular and Structural Characterization of the Biosurfactant Produced by Pseudomonas aeruginosa DAUPE 614," Chemistry and Physics of Lipids 147:1-13 (2007).
Zhang et al., Effect of a Pseudomonas Rhamnolipid Biosurfactant on Cell Hydrophobicity and Biodegradation of Octadecane, Appl. Environ. Microbiol. 60(6):2101-2106 (1994).
McLean et al., "Evidence of Autoinducer Activity in Naturally Occurring Biofilms," FEMS Microbiol. Ltrs. 154:259-263 (1997).
McLean et al., "Quorum Sensing and Chromobacterium violaceum: Exploitation of Violacein Production and Inhibition for the Detection of N-acylhomoserine Lactones," Microbiology 143:3703-3711 (1997).
Miller et al., "Quorum Sensing in Bacteria," Annu. Rev. Microbiol. 55:165-199 (2001).
Material Safety Data Sheet: Asiatic Acid, Sigma-Aldrich, pp. 1-5 (2010).
Jin et al., "Biofilm-Forming Ability of Candida albicans is Unlikely to Contribute to High Levels of Oral Yeast Carriage in Cases of Human Immunodeficiency Virus Infection," J. Clin. Microbiol. 41(7):2961-2967 (2003).
Marques et al., "A Fatty Acid Messenger is Responsible for Inducing Dispersion in Microbial Biofilms," J. Bacteriol. 191(5):1393-1403 (2009).

* cited by examiner

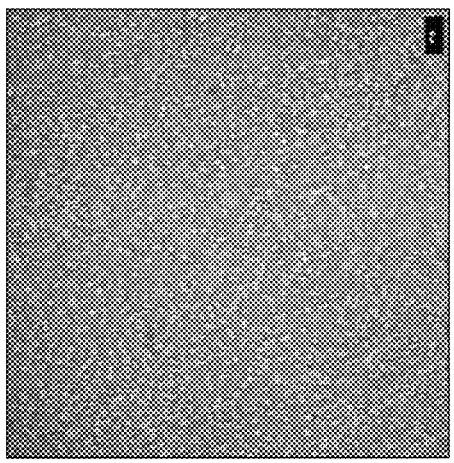
FIG. 2A  BEFORE TREATMENT
FIG. 2B  5 MIN POST TREATMENT
FIG. 2C  30 MIN POST TREATMENT

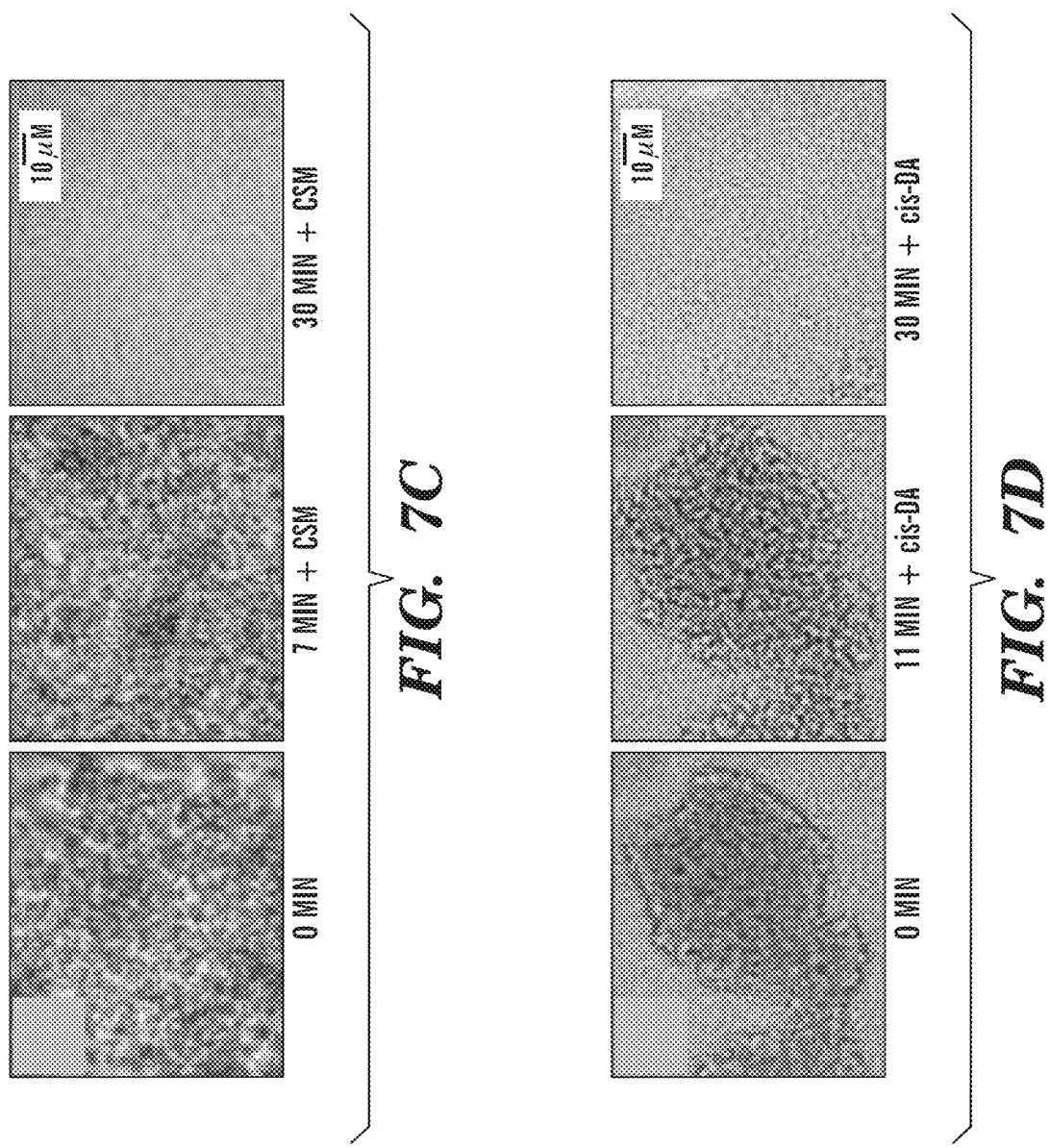

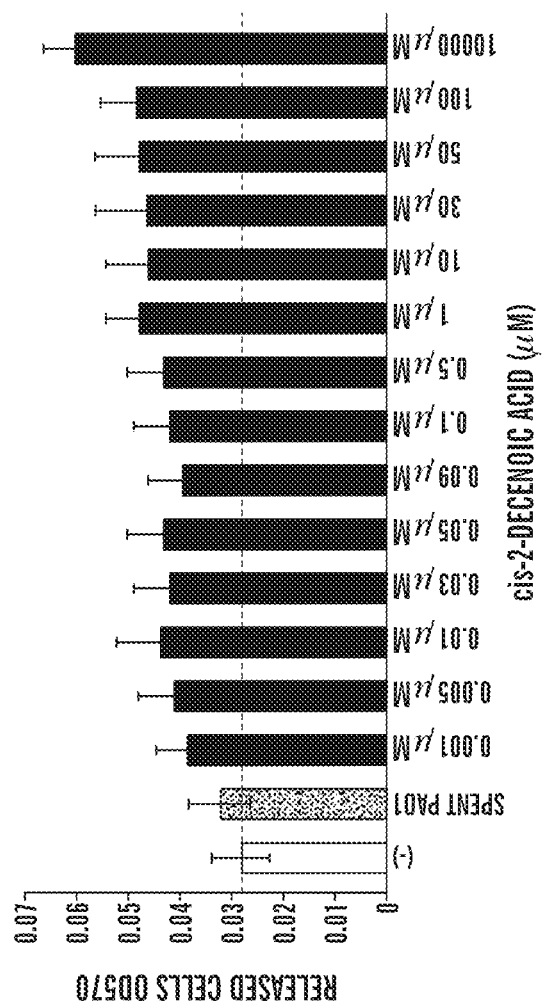
FIG. 10B
FIG. 10C

INDUCTION OF A PHYSIOLOGICAL DISPERSION RESPONSE IN BACTERIAL CELLS IN A BIOFILM

This application is a divisional of U.S. patent application Ser. No. 12/152,347, filed May 14, 2008, which claims the benefit of U.S. Provisional Patent Application Ser. Nos. 60/917,791, filed May 14, 2007, and 61/018,639, filed Jan. 2, 2008, which are hereby incorporated by reference in their entirety This invention was made with government support under grant numbers NSF MCB-0321672 and NIH R15AI055521-01 awarded by NIH and NSF. The government has certain rights in this invention.

FIELD OF THE INVENTION

The present invention is directed to a method of inducing a physiological dispersion response in bacterial cells in a biofilm.

BACKGROUND OF THE INVENTION

Due to the compact nature of biofilm structures, the presumed reduced physiological state of biofilm bacteria and the protection conferred by biofilm matrix polymers, natural and artificial chemical agents are unable to adequately attack and destroy infectious biofilm populations (Costerton et al., "Bacterial Biofilms in Nature and Disease," *Annu. Rev. Microbiol.* 41:435-464 (1987); Hoiby et al., "The Immune Response to Bacterial Biofilms," In *Microbial Biofilms*, Lappin-Scott et al., eds., Cambridge: Cambridge University Press (1995)). Increased antibiotic resistance is a general trait associated with biofilm bacteria. When attached, bacteria exhibit a profound resistance, rendering biofilm cells 10-1000 fold less susceptible to various antimicrobial agents than the same bacterium grown in planktonic (free floating) culture. For instance, chlorine (as sodium hypochlorite) an oxidizing biocide considered to be one of the most effective antibacterial agents, has been shown to require a 600 fold increase in concentration to kill biofilm cells of *Staphylococcus aureus* when compared to planktonic cells of the same species (Luppens et al., "Development of a Standard Test to Assess the Resistance of *Staphylococcus aureus* Biofilm Cells to Disinfectants," *Appl Environ Microbiol.* 68:4194-200 (2002)). Several hypotheses have been advanced to account for the extraordinary resistance of biofilm bacteria to antibiotics including: (i) reduced metabolic and divisional rates exhibited by biofilm bacteria (particularly those deep within the biofilm); (ii) the biofilm EPS matrix may act as an adsorbent or reactant, reducing the amount of agent available to interact with biofilm cells. Additionally, the biofilm structure may physically reduce the penetration of antimicrobial agents by walling off access to regions of the biofilm; (iii) biofilm cells are physiologically distinct from planktonic bacteria, expressing specific protective factors such as multidrug efflux pumps and stress response regulons (Brown et al., "Resistance of Bacterial Biofilms to Antibiotics: A Growth-Rate Related Effect?" *J. Antimicrob. Chemotherapy* 22:777-783 (1988); Anwar et al., "Establishment of Aging Biofilms: Possible Mechanism of Bacterial Resistance to Antimicrobial Therapy," *Antimicrob. Agents Chemother.* 36:1347-1351 (1992); Mah et al., "Mechanisms of Biofilm Resistance to Antimicrobial Agents," *Trends Microbiol.* 9:34-39 (2001); Sauer et al., "*Pseudomonas aeruginosa* Displays Multiple Phenotypes During Development as a Biofilm," *J. Bacteriol.* 184:1140-1154 (2002); Stewart, P. S., "Mechanisms of Antibiotic Resistance in Bacterial Biofilms," *Int. J. Med. Microbiol.* 292:107-113 (2002); Donlan et al., "Biofilms: Survival Mechanisms of Clinically Relevant Microorganisms," *Clinical Microbiol. Reviews* 15:167-193 (2002); Gilbert et al., "The Physiology and Collective Recalcitrance of Microbial Biofilm Communities," *Adv. Microb. Physiol.* 46:202-256 (2002); Gilbert et al., "Biofilms In vitro and In vivo: Do Singular Mechanisms Imply Cross-Resistance?" *J. Appl. Microbiol. Suppl.* 98S-110S (2002)). As detailed molecular studies emerge, it is becoming apparent that each of these factors plays a role in the unusual resistance of biofilms to antimicrobials. Initial treatment is usually effective in killing bacteria only at the margins of biofilm microcolonies. Bacteria deep within these microcolonies are unaffected by the antibiotic and form a nidus for continued dissemination of the infection.

Microbial biofilms in infections and in industrial systems present significant problems due to their recalcitrance to effective treatment.

Detachment is a generalized term used to describe the removal of cells (either individually or in groups) from a biofilm or substratum. Bryers, J. D., "Modeling Biofilm Accumulation," In: *Physiology Models in Microbiology*. Bazin et al., eds., Boca Raton, Fla., Vol. 2, pp. 109-144 (1988) categorized four distinct detachment mechanisms by which bacteria detach from a biofilm. These are: abrasion, grazing, erosion, and sloughing. These mechanisms have been described principally from the point of view of the chemical and physical environment acting upon biofilm bacteria. Active detachment as a physiologically regulated event has been hinted at by many authors, but few studies have been performed to demonstrate a biological basis for detachment of bacteria from a biofilm.

One study on the physiological regulation of detachment was carried out by Peyton et al., "Microbial Biofilms and Biofilm Reactors," *Bioprocess Technol.* 20:187-231 (1995) on *P. aeruginosa*. In their work, it was observed that substrate limitation resulted in a decrease in the detachment rate, presumably a result of reducing the growth rate. Allison et al., "Extracellular Products as Mediators of the Formation and Detachment of *Pseudomonas fluorescens* Biofilms," *FEMS Microbiol. Lett.* 167:179-184 (1998) showed that following extended incubation, *P. fluorescens* biofilms experienced detachment, coincident with a reduction in EPS. In *Clostridium thermocellum*, the onset of stationary phase has been correlated with increased detachment from the substratum (Lamed et al., "Contact and Cellulolysis in *Clostridium thermocellum* via Extensive Surface Organelles," *Experientia* 42:72-73 (1986)). It has been postulated that starvation may lead to detachment by an unknown mechanism which allows bacteria to search for habitats richer in nutrients (O'Toole et al., "Biofilm Formation as Microbial Development," *Ann. Rev. Microbiol.* 54:49-79 (2000)).

The transition from a flowing system to a batch culture system has been observed by many labs to result in biofilm detachment. One lab has observed reproducible detachment of biofilm cells of *P. aeruginosa* when flow is arrested in a continuous culture system (Davies, D. G., "Regulation of Matrix Polymer in Biofilm Formation and Dispersion," In *Microbial Extracellular Polymeric Substances*, pp. 93-112, Wingender et al., eds., Berlin: Springer (1999)).

The release of degradative enzymes has been proposed by others. One such example is found with the gram positive organism *Streptococcus mutans* which 30 produces a surface protein releasing enzyme (SPRE), shown to mediate the release of proteins from the cell envelope (Lee et al., "Detachment of *Streptococcus mutans* Biofilm Cells by an Endogenous Enzymatic Activity," *Infect. Immun.* 64:1035-1038 (1996)). Boyd et al., "Role of Alginate Lyase in Cell Detachment of *Pseudomonas aeruginosa*," *Appl. Environ. Microbiol.* 60:2355-2359 (1995) showed that over-expression of alginate lyase causes the degradation of alginate. When a mucoid strain of *P. aeruginosa* was induced to over-express alginate lyase, cells were more easily removed by gentle rinsing from solid medium.

Cell density dependent regulation may also be responsible for the release of enzymes which can degrade biofilm matrix polymers allowing bacteria to disperse from a biofilm. It has been observed at the Center for Biofilm Engineering at Montana State University, USA (Davies, D. G. and Costerton, J. W.) and in the laboratories of Dr. Lapin-Scott at the University of Exeter, UK, that when certain bacteria (including *P. aeruginosa*) reach high cell densities in biofilm cell clusters, the bacteria often undergo a detachment event. Mutants of *P. aeruginosa* which lacked the ability to synthesize the quorum sensing autoinducer $3OC_{12}$—HSL, were susceptible to detachment following treatment with mild detergent (Davies et al., "The Involvement of Cell-to-Cell Signals in the Development of a Bacterial Biofilm," *Science* 280:295-298 (1998)). Other investigators have demonstrated that homoserine lactones may play a role in detachment. Lynch et al., "Investigation of Quorum Sensing in *Aeromonas hydrophila* Biofilms Formed on Stainless Steel: In: *Biofilms—The Good, the Bad and the Ugly*, Wimpenny et al., eds. Bioline, Cardiff. pp. 209-223 (1999) reported an increase in detachment of *Aeromonas hydrophila* from biofilms and Puckas et al., "A Quorum Sensing system in the Free-Living Photosynthetic Bacterium *Rhodobacter sphaeroides*," *J. Bacteria* 179:7530-7537 (1997) reported that homoserine lactone production was negatively correlated with cell cluster formation in *Rhodobacter sphaeroides*.

It has been recognized that *P. aeruginosa* biofilms do not develop into macroscopic biofilm structures in batch culture flasks (at the glass liquid interface). Yet, when medium is pumped continuously through such a flask, (as in a chemostat) a luxurious biofilm develops completely coating the glass surface. When flow is halted in such a system, the biofilm sloughs after a number of days, generally around 72 hrs (Davies et al., "The Involvement of Cell-to-Cell Signals in the Development of a Bacterial Biofilm," *Science* 280: 295-298 (1998)). The inability of biofilms to develop in batch culture has been observed for a number of gram negative and gram positive bacteria as well as mixed cultures of bacteria. This phenomenon demonstrates that there is some aspect of batch growth that is inhibitory to biofilm development.

During the last stage of biofilm development, the protein profile of bacteria matches more closely the protein profile of planktonic cells than it does biofilm bacteria from the previous stage, denoted maturation II (see FIG. 3 of the current application, and Sauer et al., "*Pseudomonas aeruginosa* Displays Multiple Phenotypes During Development as a Biofilm," *J. Bacteriol.* 184:1140-1154 (2002)).

Due to the compact nature of biofilm structures, the presumed reduced physiological state of biofilm bacteria and the protection conferred by biofilm matrix polymers, current natural and artificial chemical agents are unable to adequately attack and destroy infectious biofilm populations (Costerton et al., "Bacterial Biofilms in Nature and Disease," *Annu. Rev. Microbiol.* 41:435-464 (1987); Hoiby et al., "The Immune Response to Bacterial Biofilms," In *Microbial Biofilms*, Lappin-Scott et al., eds., Cambridge: Cambridge University Press (1995)).

The present invention is directed to overcoming these and other deficiencies in the art.

SUMMARY OF THE INVENTION

One aspect of the present invention is directed to a composition. The composition comprises one or more dispersion inducers having the following formula:

where ═ is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains one or more additive components selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm.

Another aspect of the present invention relates to a method of treating or preventing a condition mediated by a biofilm in a subject. The method comprises providing a subject having, or susceptible to, a condition mediated by a biofilm produced by a microorganism, whereby the biofilm comprises a matrix and the micro-organism on a surface. Administered to the subject is a dispersion inducer comprising:

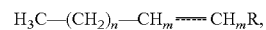

where ═ is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, the condition mediated by a biofilm in the subject is treated or prevented.

An additional aspect of the present invention relates to a method of treating or inhibiting formation of a biofilm on a surface. This method involves providing a surface having or being susceptible to formation of a biofilm produced by a microorganism, where the biofilm comprises a matrix and the micro-organism on the surface. Administered to the surface is a dispersion inducer comprising:

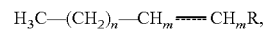

where ═ is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, formation of the biofilm on the surface is treated or inhibited.

Another aspect of the present application relates to a solution comprising:
a dispersion inducer having the following formula:

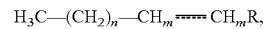

where ═ is a single or double carbon-carbon bond, m is 1 or 2, n is 4 to 7, and R is a carboxylic acid, where said inducer is present at a concentration less than 0.5 percent by weight, and where said solution has a pH greater than 5.

A further aspect of the present invention is directed to a composition comprising: a component selected from one or more of the group consisting of biocides, surfactants, antibiotics, antiseptics, detergents, chelating agents, virulence factor inhibitors, gels, polymers, pastes, edible products, and chewable products. In addition, the composition includes a dispersion inducer comprising:

$$H_3C—(CH_2)_n—CH_m\text{\textemdash\textemdash}CH_mR,$$

where 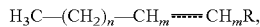 is a single or double carbon-carbon bond, m is 1 or 2, n is 4 to 7, and R is a carboxylic acid. The inducer is formulated in a non-salt form.

The present invention is also directed to a solution which includes a cis isomer of 2-decenoic acid, where the solution is selected from the group consisting of a skin cream, a toothpaste, and a mouthwash and where the solution is substantially free of the trans isomer of 2-decenoic acid.

Another form of the present application is directed to a solution comprising: a cis isomer of 2-decenoic acid, where the solution is selected from the group consisting of a skin cream, a toothpaste, and a mouthwash and where said solution is trans isomer-free.

Another form of the present application is for a method which comprises providing contact lenses and a solution comprising a dispersion inducer at a concentration less than 0.5% by weight, said inducer comprising:

$$H_3C—(CH_2)_n—CH_m\text{\textemdash\textemdash}CH_mR,$$

where  is a single or double carbon-carbon bond, m is 1 or 2, n is 4 to 7, and R is a carboxylic acid, a salt, an ester, or an amide, where the ester or amide is an isostere or biostere of the carboxylic acid. The contact lenses are then treated with said solution.

A further form of the present invention is for a method which involves providing a subject with a skin condition and a solution having a pH greater than 5, where the solution comprising a dispersion inducer at a concentration less than 0.5% by weight said inducer comprising:

$$H_3C—(CH_2)_n—CH_m\text{\textemdash\textemdash}CH_mR,$$

where 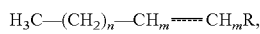 is a single or double carbon-carbon bond, m is 1 or 2, n is 4 to 7, and R is a carboxylic acid, a salt, an ester, or an amide, where the ester or amide is an isostere or biostere of the carboxylic acid. The skin condition is then treated with the solution.

Further aspects of the present invention relate to methods of: treating subjects with burns; treating and/or preventing dental plaque, dental caries, gingival disease, and oral infection; cleaning and/or disinfecting contact lenses; treating and/or preventing acne or other biofilm-associated skin infections on the skin of a subject, and treating and/or preventing a chronic biofilm-associated disease in a subject. The methods involve administering the dispersion inducer according to the present invention, under conditions effective to accomplish each respective task. Advantageously, the biofilm dispersion inducer is highly bioactive on the microorganisms within the biofilm, and, therefore, the pharmaceutically acceptable formulation need not be chemically or mechanically active to disrupt the matrix directly. Thus, the composition may have a mild pH and be non-irritating.

The present invention also relates to a composition comprising one or more dispersion inducers and one or more additive components. These additive components are selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect to disrupt the matrix.

Another aspect of the present invention relates to a method of treating or preventing a condition mediated by a biofilm in a subject. This method involves providing a subject having, or susceptible to, a condition mediated by a biofilm produced by a microorganism, whereby the biofilm comprises a matrix and the micro-organism on a surface. A dispersion inducer is administered to the subject under conditions effective for the dispersion inducer to selectively act on the microorganism and have a suitable biological response without a required direct effect on the matrix, whereby the condition mediated by a biofilm in the subject is treated or prevented.

A further embodiment of the present application is directed to a method of treating or inhibiting formation of a biofilm on a surface. This involves providing a surface having or being susceptible to formation of a biofilm produced by a microorganism, whereby the biofilm comprises a matrix and the micro-organism on the surface. A dispersion inducer is administered to the surface under conditions effective for the dispersion inducer to selectively act on the microorganism and have a suitable biological response without a required direct effect on the matrix, whereby formation of the biofilm on the surface is treated or inhibited.

The present invention addresses the "biofilm problem" by artificially inducing bacteria to undergo physiological process of biofilm dispersion. The ability to induce dispersion will allow the control of biofilms directly and will improve existing treatments with biocides, topical antibiotics, detergents, etc. The examples of situations in which artificial dispersion would be of benefit include improved cleaning of contact lenses and teeth, improved antiseptic activity in the home, in industry, and in the medical community and enhanced cidal activity for existing antibiotic treatments such as with burn patients infected with *Pseudomonas aeruginosa*.

BRIEF DESCRIPTION OF THE DRAWINGS

As shown in FIG. 1A, following treatment, only the cells on the surface of the biofilm are killed by the antibiotic. FIG. 1B is a schematic representation of a biofilm induced to disperse along with treatment with antibiotic. Dispersed cells are completely killed during the treatment.

FIGS. 2A-C depict the effect of addition of chloroform extracted spent culture medium (CSM) which contains a dispersion inducing compound, to mature biofilms of *Pseudomonas aeruginosa*. FIG. 2A shows biofilm growing in continuous culture on a glass slide in a flow cell. FIG. 2B shows the same area of biofilm 5 minutes after the addition of the dispersion inducer. FIG. 2C shows complete disaggregation of biofilm following 30 minutes initial treatment with dispersion inducer.

FIG. 4A shows early biofilm development under flowing conditions, while FIG. 4B is the same location after flow is stopped for 72 hrs.

FIGS. 7A-D show treatment of P. aeruginosa mature biofilms with spent medium, CSM and cis-2-decenoic acid. As shown in FIG. 7A, at 30 min, biofilms grown in silicone tubing were exposed to spent medium or fresh medium. Bacteria in effluent were collected continuously for 100 min and cell density determined by $OD_{600}$. As shown in FIG. 7B, biofilm grown in continuous culture in silicone tubing for 4 days and switched either to fresh medium for 1 hr, or CSM for 1 hr. Extruded contents of control tube shows intact biofilm. Extruded contents of CSM-treated biofilm shows dispersion. Photomicrographs show addition of CSM to mature biofilm grown in continuous culture in a microscope-mounted flow cell, as shown in FIG. 7C. Microcolony disaggregation is shown to begin at 7 min. After 30 min exposure, the microcolony had completely disaggregated. Dispersed cells were actively motile (not visible in static image), indicating a change in phenotype compared to cells in intact microcolony (prior to CSM addition). As shown in FIG. 7D, addition of 10 μM cis-2-decenoic acid (cis-DA) to mature biofilm grown in continuous culture in a microscope-mounted flow cell. Microcolony disaggregation is shown to begin at 11 min. Complete microcolony disaggregation is shown within 30 min exposure. Control biofilms treated with carrier fluid were not affected by treatment up to 1 hr.

FIGS. 10A-C show a microtiter plate dispersion bioassay. FIG. 10A shows optical densities of cells released from biofilm-containing microtiter plate wells. White bar, control sample treated with EPRI alone. Grey bar, sample treated with CSM. Black bars represent biofilms treated with C-18 reverse phase HPLC fractions of CSM eluted in an acetonitrile gradient from 2% to 75%. Results are the average of 16 replicate wells, error bars represent one standard deviation. Results from Student's T-test show P<0.001 for CSM and 22-minute HPLC samples. FIG. 10B shows microtiter plate biofilm dispersion bioassay comparing various concentrations of cis-2-decenoic acid to spent medium. Optical densities of cells released from biofilm-containing microtiter plate wells. Negative control wells contained P. aeruginosa treated with 10% ethanol in EPRI. Grey bar represents biofilms treated with spent medium. Black bars represent biofilms treated with increasing concentrations of cis-2-decenoic acid in 10% ethanol. Results are the average of 16 replicate wells, error bars represent one standard deviation. Student's T-test indicated P<0.001 for all cis-2-decenoic acid samples compared to control. FIG. 10C shows the structure of cis-2-decenoic acid.

FIG. 12A shows product ion mass peaks for the 171 M/Z molecule detected in active HPLC CSM fraction and for synthetic cis-2-decenoic acid. Y-axis indicates intensity; X-axis indicates M/Z in positive ion mode. CSM sample matches peaks from synthetic cis-2-decenoic acid. Note that in mass spectrometry, peak intensity is not a direct indication of concentration. FIG. 12B shows GC-MS spectrum of P. aeruginosa CSM and cis-2-decenoic acid. CSM sample Peak at 15.9 min, indicates solvent carrier. Y-axis indicates intensity; X-axis indicates time in minutes. FIG. 12C shows FT-IR spectrum of *P. aeruginosa* CSM and cis-2-decenoic acid. Y-axis indicates absorbance; X-axis indicates reciprocal centimeters.

DETAILED DESCRIPTION OF THE INVENTION

Figure 1A:
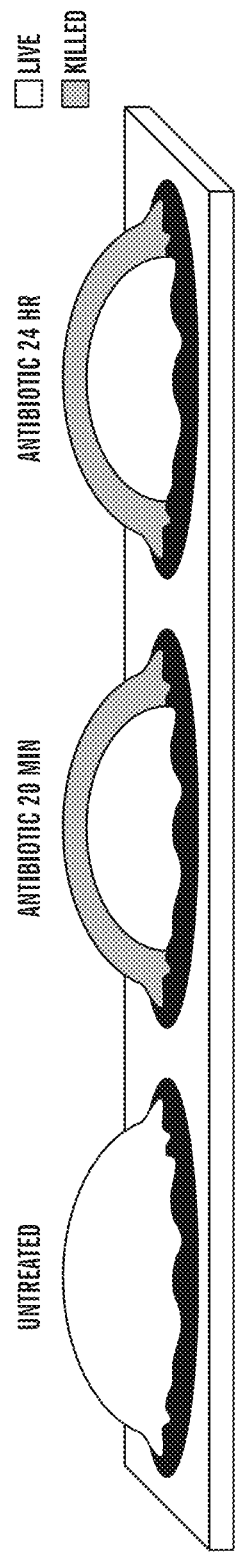
FIGS. 1A-B are schematic representations of biofilm treated with an antibiotic and/or a dispersion inducer.

One aspect of the present invention is directed to a composition. The composition includes one or more dispersion inducers comprising:

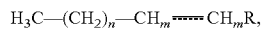

where ═ is a single or double carbon-carbon bond, m is 1 or 2, n is 2 to 15, and R is a carboxylic acid, a salt, an ester, or an amide, where the ester or amide is an isostere or biostere of the carboxylic acid. The composition additionally contains one or more additive components selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect on the matrix to disperse the biofilm. In achieving this result, the dispersion inducer of the present invention can act in preference directly on the matrix. Alternatively, the dispersion inducer can act on the microorganism which, in turn, acts to disrupt the matrix. This effect may also involve not relying on a direct effect on the matrix. Typically, the biofilm inducer will have no effect on the matrix directly or be present at a concentration where no direct effect on the matrix is evident. On the other hand, the range of effective concentrations suggest a biochemical response mechanism in the microorganisms, wherein the dispersion inducer mimics an intercellular communication composition. The composition acts to induce a dispersion response by the bacteria, which in turn is responsible for release of the bacteria from the biofilm. Additionally, the composition is able to act on bacteria not in a biofilm (planktonic bacteria), inducing these bacteria to mount a physiological response which prevents the formation of a biofilm. Additional components of a composition may be directed to disrupting or removing the matrix from the surface or substrate. For example, the composition may comprise a dentifrice adapted to abrasively remove plaque from teeth.

The R group of the above inducer may be selected from the group consisting of:

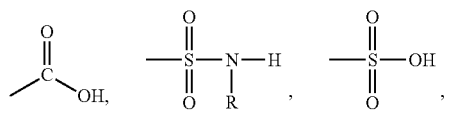

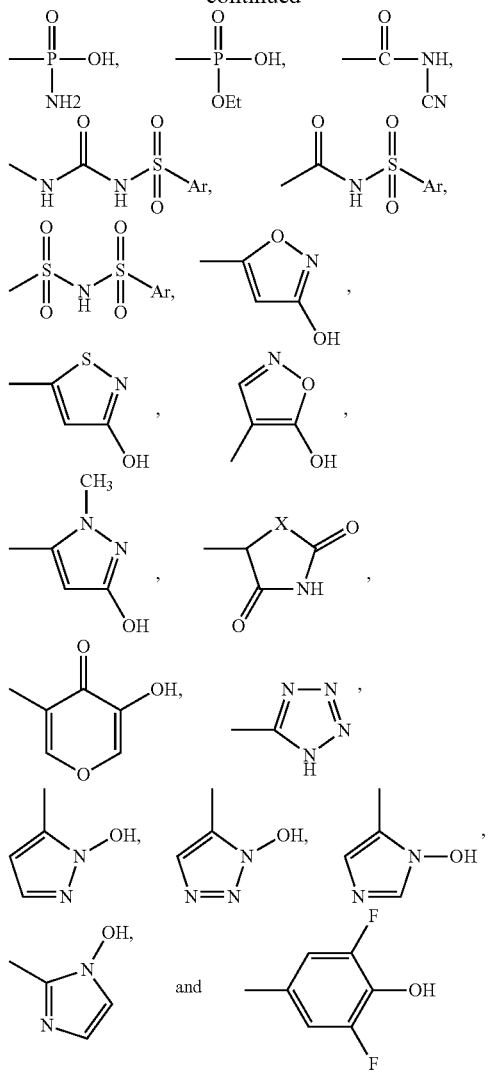

Alternatively, R can be a homoserine lactone or a furanone group. The composition also includes an additive component such as one or more of biocides, surfactants, antibiotics, antiseptics, detergents, chelating agents, virulence factor inhibitors, gels, polymers, pastes, edible products, or chewable products.

The dispersion inducer of the present invention desirably comprises 7-10 carbon atoms. It is preferred that this inducer be a carboxylic acid (e.g., a monounsaturated fatty acid). It is more preferred that the dispersion inducer comprise:

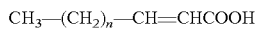

Suitable non-salt forms of this dispersion inducer being the following respective cis- and trans-isomers:

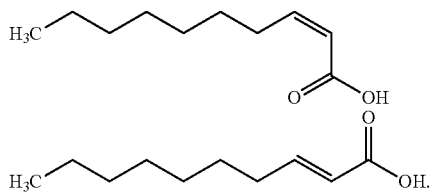

Of these, the cis isomer is preferred.

Other suitable alkanoic acids include hexanoic acid, heptanoic acid, octanoic acid, nonanoic acid, decanoic acid, undecanoic acid, dodecanoic acid, tridecanoic acid, tetradecanoic acid, pentanoic acid, hexadecanoic acid, heptadecanoic acid, octadecanoic acid, and nonadecanoic acid.

Useful alkenoic acids include 2-hexenoic acid, 2-heptenoic acid, 2-octenoic acid, 2-nonenoic acid, 2-undecenoic acid, 2-dodecenoic acid, 2-tridecenoic acid, 2-tetradecenoic acid, 2-pentadecenoic acid, 2-hexadecenoic acid, 2-heptadecenoic acid, 2-octadecenoic acid, and 2-nonadecenoic acid. These may be cis or trans isomers.

The composition of the present invention can be formulated at a number of pH ranges, to treat different types of bacteria, as follows: 1.5 to 4.5 for acid loving bacteria; 4.5 to 8.0 for acid tolerant bacteria; 6.8 to 7.4 for substantially neutral pH loving bacteria; and 8.0 to 9.8 for alkali tolerant bacteria. An essentially neutral pH is particularly desirable for subjects with acid reflux. The concentration of the dispersion inducer can be 0.01 μM to 30 mM.

The composition can be entirely or substantially (i.e. less than 10 wt %) ethanol free and/or formaldehyde free.

A surface (or substrate) coated with the composition is also encompassed by the present invention.

Another aspect of the present invention relates to a method of treating or preventing a condition mediated by a biofilm in a subject. The method comprises providing a subject having, or susceptible to, a condition mediated by a biofilm produced by a microorganism, whereby the biofilm comprises a matrix and the micro-organism on a surface. Administered to the subject is a dispersion inducer comprises:

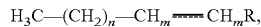

where ═ is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, the condition mediated by a biofilm in the subject is treated or prevented. The method of dispersing the biofilm may further include administering to the biofilm, in conjunction with administering the dispersion inducer, an antimicrobial treatment. The treatment can be the administration of biocides (e.g., hydrogen peroxide), surfactants, antibiotics, antiseptics, detergents, chelating agents, virulence factor inhibitors, gels, polymers, pastes, edible products, chewable products, ultrasonic treatment, radiation treatment, thermal treatment, and/or mechanical treatment.

An additional aspect of the present invention relates to a method of treating or inhibiting formation of a biofilm on a surface. This method involves providing a surface having or being susceptible to formation of a biofilm produced by a microorganism, where the biofilm comprises a matrix and the micro-organism on the surface. Administered to the surface is a dispersion inducer comprising:

where ═ is a single or double carbon-carbon bond, m is 1 or 2, n is 2 to 15, and R is a carboxylic acid, a salt, an ester, or an amide, where the ester or amide is an isostere or biostere of the carboxylic acid, under conditions effective for the dispersion inducer to selectively act on the microorganism and have a suitable biological response without a required direct effect on the matrix. As a result, formation of the biofilm on the surface is treated or inhibited.

In one embodiment, the surface to be treated includes indwelling medical devices, such as catheters, respirators, and ventilators. In addition, the surface can be in implanted medical devices, including stents, artificial valves, joints, pins, bone implants, sutures, staples, pacemakers, and other temporary or permanent devices. The dispersion inducer of the present invention can also be included in surgical glue. In another embodiment, the surface to be treated includes drains, tubs, kitchen appliances, countertops, shower curtains, grout, toilets, industrial food and beverage production facilities, flooring, and food processing equipment. In a further embodiment, the surface to be treated is a heat exchanger surface or a filter surface. Thus, treatment provides a means for reducing the degree of bio fouling of the heat exchanger or filter. In a final embodiment, the surface to be treated is a marine structure which includes boats, piers, oil platforms, water intake ports, sieves, and viewing ports. The surface can alternatively be associated with a system for water treatment and/or distribution (e.g., a system for drinking water treatment and/or distributing, a system for pool and spa water treatment, a system for treatment and/or distribution of water in manufacturing operations, and a system for dental water treatment and/or distribution). The surface can also be associated with a system for petroleum drilling, storage, separation, refining and/or distribution (e.g., a petroleum separation train, a petroleum container, petroleum distributing pipes, and petroleum drilling equipment). The dispersion inducer can also be included in formulations directed at reducing or eliminating biofilm deposits or bio fouling in porous medium, such as with oil and gas bearing geological formations. The treatment may be accomplished by applying a coating, such as paint, to the surface.

The method of inhibiting formation of a biofilm on a surface may further involve administering to the surface, in conjunction with administering the dispersion inducer, an antimicrobial treatment. The treatment can be administration of biocides, surfactants, antibiotics, antiseptics, disinfectants, medicines, detergents, chelating agents, virulence factor inhibitors, ultrasonic treatment, radiation treatment, thermal treatment, and mechanical treatment. In one embodiment, the dispersion inducer and the antimicrobial treatment are administered simultaneously. In another embodiment, the dispersion inducer and antimicrobial treatment are administered separately.

The dispersion inducer can be impregnated in a surface in order to inhibit formation of a biofilm on the surface. Alternatively, the dispersion inducer can be in a copolymer or a gel coating over the surface.

The present invention also relates to a method of treating subjects with burns. The method involves administering the dispersion inducer according to the present invention, under conditions effective to treat burns in the subject. A specific application of the invention provides a topical dressing for burn patients comprising dispersion inducing molecules or their natural or synthetic analogs to prevent the development of infectious biofilms or to disperse the cells of existing infectious biofilms.

The present invention further relates to a method of treating and/or preventing dental plaque, dental carries, gingival disease, periodontal disease, and oral infection in a subject. The method involves treating the oral cavity of the subject with the dispersion inducer according to the present invention. Treating can be carried out with a dentifrice, mouthwash, dental floss, gum, strip, toothpaste, a toothbrush containing the dispersion inducer, and other preparations containing the dispersion inducer. The composition may also contain other compounds known in the dental arts that are typically added to dental compositions. For example, the dispersion inducer composition may also include fluoride, desensitizing agents, anti-tartar agents, anti-bacterial agents, remineralization agents, whitening agents, and anti-caries agents.

The amount of dispersion inducer present will vary dependent on the dental composition that contains the dispersion inducer. It has been found that the dispersion inducer is active over a wide range of concentrations against oral bacteria. For instance, the dispersion inducer may be present in an amount ranging from 0.1 nM to 10 mM. However, lower and higher concentrations may be used depending on the dental composition, the other components present in the dispersion inducer composition, and various other factors appreciated by those of skill in the art. The known properties of the dispersion inducer, such as its fatty acid characteristics and its hydrophobicity, will assist a skilled artisan in determining how much of the dispersion inducer should be used, determining how the compound will chemically interact with other components, and providing other useful information about the compound.

Specific dental applications and dental compositions are contemplated in this invention. In this regard, the invention relates to a toothbrush containing a dispersion inducer composition. Toothbrushes, as is well known in the art, contain a plurality of bristles and a solid support on which the bristles are mounted, where the solid support includes a brush head having a plurality of tuft holes that receive the bristles. Variations and modifications of the basic toothbrush are well known in the art. See, for example, U.S. Pat. No. 7,251,849, herein incorporated by reference in its entirety.

The dispersion inducer of this invention has a chemical formula as set forth above. Additional components that may be included in the dispersion inducer compositions are also set forth above. The dispersion inducer composition may be incorporated in the various parts of the toothbrush by means known in the art. For instance, the dispersion inducer composition may be contained in the tuft holes of the toothbrush. See U.S. Pat. No. 5,141,290, herein incorporated by reference in its entirety, for an example of how a composition can be contained within the tuft holes of a toothbrush. Alternatively, the dispersion inducer composition may be coated or embedded in the bristles of the toothbrush.

Other parts of the toothbrush may also be coating or embedded with the dispersion inducer composition, including any parts of the toothbrush that supplement the bristles and are designed to be contacted with the oral cavity. For example, it is common for toothbrushes to contain rubber paddles, tongue cleaners, or other pieces extended from the head for the purposes of being contacted with the tooth, tongue, gums, or other areas of the oral cavity. These parts may be embedded with the dispersion inducer composition and, optionally, a surfactant, biocide, and/or other additive discussed above.

To assist in controlling the release of the dispersion inducer from the toothbrush, the dispersion inducer composition may contain an agent that interacts with the dispersion inducer to assist in the controlled release. The agent may interact with the dispersion inducer in a manner that the release is either accelerated or prolonged, depending on the desired use. The level of controlled release can also depend on how easily or difficult the dispersion inducer adheres to the portion of the toothbrush that it is applied to. In a preferred embodiment, the dispersion inducer is slowly released from the toothbrush over repeated brushings. Agents that enable the slow release of an active ingredient are well known to those of skill in the art.

The controlled release may also be effectuated by encapsulating the dispersion inducer in an encapsulated system that allows a controlled release. In this embodiment, the dispersion inducer composition is preferably in the form of a plurality of small microspheres that encapsulate the dispersion inducer. The microspheres can have an outer coating of dissolvable material that enables the dispersion inducer to slowly release over repeated brushings. Suitable microspheres include those disclosed in U.S. Pat. No. 5,061,106, herein incorporated by reference in its entirety.

This invention also relates to a toothpaste composition that contains (a) fluoride and/or a remineralization agent; (b) an orally-accepted vehicle; and (c) a dispersion inducer composition. The dispersion inducer of this invention has a chemical formula as set forth above. Additional components that may be included in the dispersion inducer compositions are also set forth above. Often, toothpastes also contain sodium lauryl sulfate or other sulfates.

Fluoride in its various forms is a common active ingredient in toothpaste to prevent cavities and promote the formation of dental enamel and bones. Any fluoride source, such as fluoride salts may be used in the toothpaste of this invention. Preferably, the fluoride is sodium fluoride (NaF) or sodium monofluorophosphate ($Na_2PO_3F$). Typically, the amount of fluoride present in the toothpaste ranges from 100 to 5000 parts per million fluoride ion, preferably 1000 to 1100 parts per million.

In certain instances, it is preferable to replace or supplement the fluoride with a remineralization agent. Remineralization, in the context of dental usage, generally refers to treating the teeth so as to prevent dental caries, or decrease their chance of occurring, and otherwise enhance the teeth so that they can return to their original, healthy state. While fluoride can be considered a remineralization agent, other agents often take the place of fluoride or supplement fluoride to provide the toothpaste with a stronger cleansing or remineralization properties. Common remineralization agents are calcium salts, such as calcium phosphate, calcium sulfate, anhydrous calcium sulfate, calcium sulfate hemihydrate, calcium sulfate dihydrate, calcium malate, calcium tartrate, calcium malonate, and calcium succinate. Hydroxyapitate nanocrystals and zinc compounds have also been shown to be effective remineralization agents.

The orally-accepted vehicle may be any vehicle known in the art that can be used to deliver the fluoride and/or remineralization agent, and dispersion inducer to the teeth of a patient. The orally-accepted vehicle may also be glycerin, propylene glycol, polyethylene glycol, triglyceride, diglyceride, mineral oil, organic oils, essential oils, fatty vegetable oils, and combinations thereof. Often these vehicles are used in combination with water or a water-based solvent.

The toothpaste composition may contain other components of toothpastes well known in the art. For instance, the toothpaste composition may contain baking soda, enzymes, vitamins, herbs, calcium compounds such as calcium sodium phosphosilicate, coloring agents, and/or flavoring agents. Desensitizing agents may also be added. As known in the art, desensitizing agents can reduce sensitivity in teeth by treating sensitivities caused by demineralization or suppressing the sensitivity symptoms by desensitizing the nerves. The composition may also contain an antibacterial or an antiplaque agent. Antibacterial agents are preferable included in the composition to prevent gingivitis, periodontitis, and other oral diseases. Suitable antibacterial agents include triclosan, zinc chloride, chlorhexidine, benzthonium chloride, and cetyl pyridinium chloride.

This invention also relates to an oral composition for treating and/or preventing dental plaque, gingival diseases, periodontal diseases, and/or oral infection. The oral composition contains an orally-accepted vehicle and a dispersion inducer composition. The dispersion inducer of this invention has a chemical formula as set forth above. Additional components that may be included in the dispersion inducer compositions are also set forth above.

The oral composition can be various compositions in the field of dental hygiene known to those in the art. For instance, the oral composition may be a mouthwash, breath spray, dentifrice, tooth powder, whitening strips, or prophylaxis paste. As is well known in the art, mouthwashes are commonly used to help remove mucous and food particles in the oral cavity or throat. Mouthwashes typically contain antiseptic and/or anti-plaque components to kill the bacterial plaque that causes caries, gingivitis, and bad breath. They can also contain anti-cavity components, such as fluoride, to protect against tooth decay. Suitable mouthwash components may be found in U.S. Pat. No. 5,968,480, herein incorporated by reference in its entirety.

Likewise, the same or similar antiseptic, anti-plaque, and anti-cavity components can be used in breath sprays, dentifrices, including gel dentifrices, tooth powders, whitening strips, and prophylaxis pastes. Suitable breath spray compositions are disclosed in U.S. Pat. No. 7,297,327; suitable tooth powder compositions, such as those used in tooth bleaching compositions, are disclosed in U.S. Pat. No. 5,989,526; suitable whitening strips are disclosed in U.S. Pat. No. 6,514,483; and suitable dentifrices and prophylaxis paste compositions, including dental abrasives, are disclosed in U.S. Pat. No. 5,939,051, all of which are herein incorporated by reference in their entirety.

The ingredients of orally-accepted vehicle are similar to those discussed above. However, the orally-accepted vehicle will vary depending on the desired consistency and desired end product of the oral composition. For instance, a mouthwash is in a liquid form, so liquid carriers, typically carriers having a high percentage of water, should be used. On the other hand, a gel dentifrice should be in the form of a gel and would utilize gelling agents or other carriers that enable the final product to be in the form of a gel. The orally-accepted vehicle should have properties that both allow the dispersion inducer composition to be delivered while also providing the final product with the desired consistency.

The oral composition may also be in the form of chewing gum, a breath strip, a lozenge, or a breath mint. Chewing gum is typically a combination of a water-insoluble phase, or gum base, and a water-soluble phase of sweeteners, flavoring and/or food coloring. Other components may also be added to the gum, including breath-freshening additives such as zinc and phosphate salts, teeth-whitening additives such as silica, and plaque-reducing additives to moderate dental plaque. Suitable gum compositions may be found in U.S. Pat. Nos. 6,416,744 and 6,592,849, both of which are herein incorporated by reference in their entirety.

Breath strips are similar to chewing gum, except that the strips are designed to dissolve in the mouth, often absorbed through the tongue. The strips can deliver bioactive ingredients to freshen the mouth as well functional bioactive ingredients, such as vitamins, minerals, supplements, pharmaceuticals, and vaccines.

Lozenges and breath mints are typically discoid-shaped solids that contain a therapeutic agent in a flavored base. The base may be a hard sugar candy, glycerinated gelatin or combination of sugar with sufficient mucilage to give the composition requisite form. The dispersion inducer may represent the therapeutic agent, or it may be added in addition to therapeutic agents known in the art. Suitable lozenge and breath mint compositions are disclosed in U.S. Pat. No. 7,025,950, herein incorporated by reference in its entirety.

The oral composition may also be in the form of a cleaning preparation for a dental apparatus that is placed in the oral cavity. Dental apparatuses such as dentures, dental dams, and certain types of orthodontic braces are placed in the oral cavity for a period of time, and then periodically removed for cleaning. The cleaning composition used to clean the dental apparatuses should function in its customary manner of cleaning the apparatus, but may also contain therapeutic agents that can assist in treating or preventing dental plaque, gingival diseases, periodontal diseases, and oral infection when the dental apparatuses are in contact with the oral cavity. Cleaning compositions such as effervescent cleansers made with alkaline mixtures containing a chlorine compounds and the like are known in the art. Suitable cleaning compositions for dental apparatuses are disclosed in U.S. Pat. No. 3,936,385, herein incorporated by reference in its entirety. The dispersion inducer may be added to the cleaning compositions in a manner than enables it to coat the dental apparatus upon contact. After the dental apparatus has been introduced into the oral cavity, the dispersion inducer can interact with the teeth and other elements of the oral cavity in a therapeutically effective manner, i.e. to prevent dental plaque, gingival diseases, periodontal diseases, and/or oral infection.

This invention also relates to an article for oral use comprising a dental article and a dispersion inducer. The dispersion inducer has the chemical formula set forth above, and is coated on, encapsulated in, or impregnated in the dental article. Additional components that may be included in the dispersion inducer compositions are also set forth above.

Various dental articles known in the art may used in this embodiment of the invention. In one embodiment, the dental article is a dental floss. Any fiber known in the art may be used in the dental floss. Suitable fibers include polyamides (such as nylon), polyesters, polypropylenes, polytetrafluoroethylenes, cellulose, and cotton. Nylon and polytetrafluoroethylene fibers are the most common fibers used in dental floss and represent preferred fibers. Suitable dental flosses are disclosed in U.S. Pat. Nos. 6,270,890 and 6,289,904, both of which are herein incorporated by reference in their entirety. The dispersion inducer composition may be impregnated into the fiber, coated on the fiber, or otherwise incorporated into the dental floss.

The dental floss may be coated or impregnated with a wax or other hydrophobic substance for ease of use during the flossing process. Suitable waxes include microcrystalline waxes, beeswax, paraffin waxes, carnauba waxes, and polyethylene waxes. The dispersion inducer composition may be coated onto the dental floss as part of the wax layer, as a second or additional layer in conjunction with the wax layer, or applied to the fiber as discussed above.

The dental article may be a toothpick that is impregnated with or coated with the dispersion inducer composition. Toothpicks may be made from natural products, such as wood, or artificial components, including various plastics. Suitable toothpicks are disclosed in U.S. Pat. No. 7,264,005, herein incorporated by reference in its entirety.

The dental article may also be a dental appliance such as a dental aspirator, bite block, dental dam, tongue stabilizer, tongue deflector, or any other piece of dental equipment that a dentist or dental assistant may use in the mouth of a patient. A discussion of dental appliances may be found in U.S. Pat. Nos. 4,865,545 and 5,152,686, both of which are herein incorporated by reference. The portion of the dental appliance that comes into contact with the oral cavity of a patient may be coated with the dispersion inducer composition.

The dental article may also be a dental construct, such as a veneers, crowns, inlays, onlays, or bridges that are placed on the teeth. Dental constructs are typically made of metal alloys, porcelain, ceramic, amalgam, acrylate polymers, or a combination of these materials. Suitable dental constructs are disclosed in U.S. Pat. No. 7,229,286, herein incorporated by reference in its entirety. The dispersion inducer composition may be embedded in the composition used to make the dental construct. Alternatively, the dispersion inducer composition may be coated on the dental construct after it has been prepared.

This invention also relates to an aqueous composition applied to the oral cavity with the use of a dental article, comprising water and a dispersion inducer composition. Various dental articles are attached to or designed to be used with a water line so that water can be distributed through the dental article, and then routed from the dental article to the oral cavity of a subject. Suitable dental articles include dental water lines, dental water picks, and the like.

While tap water or purified water may be used in these type of dental devices, the water source may also be supplemented with additives so that the water delivers the additives to the oral cavity of the subject when used with the dental article. In this case, the additive supplemented to the water is a dispersion inducer composition.

Dental water lines and dental water picks are known in the art and commonly used by dentists and dental assistants. A discussion of different types of dental water lines and their different applications may be found in U.S. Pat. No. 5,785,523, herein incorporated by reference in its entirety. Suitable water picks are disclosed in U.S. Pat. No. 4,257,433, herein incorporated by reference in its entirety.

The present invention also relates to a method of cleaning and/or disinfecting contact lenses. The method involves treating contact lenses with a cleaning and/or disinfecting solution containing the dispersion inducer according to the present invention. The contact lens may be treated in this manner while being stored in solution or while being used in vivo. Alternatively, the dispersion inducer can be used in eye drops.

The present invention further relates to a method of treating and/or preventing acne or other biofilm-associated skin infections on the skin of a subject. The method involves treating the skin of the subject with the dispersion inducer according to the present invention under conditions effective to treat and/or prevent the acne or biofilm-associated skin infections. The dispersion inducer may be present in an ointment, cream, liniment, salves, shaving lotion, or aftershave. It may also be present in a powder, cosmetic, ointment, cream, liquid, soap, gel, cosmetic applicator, and/or solid, woven or non-woven material intended to contact or be proximate with the skin.

The present invention also relates to a method of treating and/or preventing a chronic biofilm-associated disease in a subject. The method involves administering to the subject the dispersion inducer according to the present invention under conditions effective to treat and/or prevent the chronic biofilm-associated disease. The chronic biofilm-associated diseases to be treated and/or prevented include, but are not limited to, middle ear infections, osteomyelitis, prostatitis, colitis, vaginitis, urethritis, arterial plaques, sinovial infections, infections along tissue fascia, respiratory tract infections (e.g., infections associated with lung infections of cystic fibrosis patients, pneumonia, pleurisy, pericardial infections), genito-urinary infections, and gastric or duodenal ulcer infections. For gastric or duodenal ulcers caused by *Helicobacter pylori*, the dispersion inducer will need to function at a pH of below 5.5. The dispersion inducer may be administered in combination with an antimicrobial agent, such as biocides, surfactants, antibiotics, antiseptics, detergents, chelating agents, or virulence factor inhibitors. In the case of gastric therapies, acid reducing therapies, such as antacids, proton pump inhibitors, antihistamines, and the like may also be employed.

Another aspect of the present application relates to a solution comprising:

a dispersion inducer comprises:

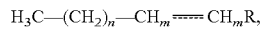

$$H_3C—(CH_2)_n—CH_m\text{═══}CH_mR,$$

where ═══ is a single or double carbon-carbon bond, m is 1 or 2, n is 4 to 7, and R is a carboxylic acid, where said inducer is present at a concentration less than 0.5 percent by weight, and where said solution has a pH greater than 5.

A further aspect of the present invention is directed to a composition comprising: a component selected from one or more of the group consisting of biocides, surfactants, antibiotics, antiseptics, detergents, chelating agents, virulence factor inhibitors, gels, polymers, pastes, edible products, and chewable products. In addition, the composition includes a dispersion inducer comprises:

$$H_3C—(CH_2)_n—CH_m\text{═══}CH_mR,$$

where ═══ is a single or double carbon-carbon bond, m is 1 or 2, n is 4 to 7, and R is a carboxylic acid. The inducer is formulated in a non-salt form.

The present invention is also directed to a solution which includes a cis isomer of 2-decenoic acid, where the solution is selected from the group consisting of a skin cream, a toothpaste, and a mouthwash and where the solution is substantially free of the trans isomer of 2-decenoic acid. As interpreted herein, this solution is substantially free of a trans isomer if a reduction in trans isomer (without change in cis-isomer) concentration does not increase bioactivity. It is more preferred that there be a molar ratio of cis to trans of at least 2.

Another form of the present application is directed to a solution comprising: a cis isomer of 2-decenoic acid, where the solution is selected from the group consisting of a skin cream, a toothpaste, and a mouthwash and where said solution is trans isomer-free.

Another form of the present application is for a method which comprises providing contact lenses and a solution comprising a dispersion inducer at a concentration less than 0.5% by weight, said inducer comprises:

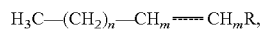

$$H_3C—(CH_2)_n—CH_m\text{═══}CH_mR,$$

where ═══ is a single or double carbon-carbon bond, m is 1 or 2, n is 4 to 7, and R is a carboxylic acid, a salt, an ester, or an amide, where the ester or amide is an isostere or biostere of the carboxylic acid. The contact lenses are then treated with said solution.

A further form of the present invention is for a method which involves providing a subject with a skin condition and a solution having a pH greater than 5, where the solution comprising a dispersion inducer at a concentration less than 0.5% by weight said inducer comprises:

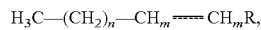

$$H_3C—(CH_2)_n—CH_m\text{═══}CH_mR,$$

where ━ is a single or double carbon-carbon bond, m is 1 or 2, n is 4 to 7, and R is a carboxylic acid, a salt, an ester, or an amide, where the ester or amide is an isostere or biostere of the carboxylic acid. The skin condition is then treated with the solution.

The present invention also relates to a composition comprising one or more dispersion inducers and one or more additive components. These additive components are selected from the group consisting of biocides, surfactants, antibiotics, antiseptics, detergents, chelating agents, virulence factor inhibitors, gels, polymers, pastes, edible products, and chewable products. The composition is formulated so that when it is contacted with a biofilm produced by a microorganism, where the biofilm comprises a matrix and microorganism on a surface, the dispersion inducer selectively acts on the microorganism and has a suitable biological response without a required direct effect to disrupt the matrix.

Another aspect of the present invention relates to a method of treating or preventing a condition mediated by a biofilm in a subject. This method involves providing a subject having, or susceptible to, a condition mediated by a biofilm produced by a microorganism, whereby the biofilm comprises a matrix and the micro-organism on a surface. A dispersion inducer is administered to the subject under conditions effective for the dispersion inducer to selectively act on the microorganism and have a suitable biological response without a required direct effect on the matrix, whereby the condition mediated by a biofilm in the subject is treated or prevented.

A further embodiment of the present application is directed to a method of treating or inhibiting formation of a biofilm on a surface. This involves providing a surface having or being susceptible to formation of a biofilm produced by a microorganism, whereby the biofilm comprises a matrix and the micro-organism on the surface. A dispersion inducer is administered to the surface under conditions effective for the dispersion inducer to selectively act on the microorganism and have a suitable biological response without a required direct effect on the matrix, whereby formation of the biofilm on the surface is treated or inhibited.

EXAMPLES

The following examples are provided to illustrate embodiments of the present invention but are by no means intended to limit its scope.

Example 1—Bacterial Strains and Media

The microorganisms used in this study included *Pseudomonas aeruginosa* PAO1 from B. H. Holloway, *Escherichia coli* (ATCC 10798), *Proteus mirabilis* (ATCC 25933), *Klebsiella pneumoniae* (ATCC 10273), *Staphylococcus aureus* (ATCC 12602), *Streptococcus pyogenes* (ATCC 19615), *Bacillus subtilis* (ATCC 6633), and *Candida albicans* (ATCC 20260) and a mixed undefined culture collected on R2A plates via airborne contamination. Except where indicated, all experiments were performed in modified EPRI medium, containing 0.005% ammonium nitrate, 0.00019% $KH_2PO_4$, 0.00063% $K_2HPO_4$ (pH 7.0), and 0.001% Hutner salts (Cohen-Bazire et al., *J. Cell. Comp. Physiol.* 49:35 (1957), which is hereby incorporated by reference in its entirety), supplemented with 0.2% glucose. *C. albicans* was grown in modified EPRI medium supplemented with 0.2% glucose and 0.1% peptone. *K. pneumoniae, P. mirabilis, S. aureus*, and *B. subtilis* were grown in modified EPRI medium supplemented with 0.1% peptone. *S. pyogenes* was grown in 10% Brain Heart Infusion broth.

Example 2—Preparation of *P. aeruginosa* Spent Medium

To prepare cell-free spent culture medium, 6 mL of an overnight culture of *P. aeruginosa* PAO1 grown in modified EPRI medium at 30° C. were inoculated into four liters of modified EPRI medium and incubated for 10 days at room temperature with continuous stirring. Bacterial cells were sedimented by centrifugation (Sorvall RC 5B Plus Centrifuge, GSA Rotor; Thermo Electron Co., Ashville, N.C.) at 13,000×g for 15 minutes at 4° C. The supernatant was removed and filtered under vacuum through a 0.45 µm Millipore Type HA filter (Millipore. Co., Billerica, Mass.) and subsequently, through a 0.2 µm, Acrodisc 32 mm syringe filter (PALL Co., East Hills, N.Y.). Spent medium was stored at 4° C.

Example 3—Preparation of CSM

The organic components of spent medium were extracted by adding 80 mL of chloroform to 250 mL of filtered spent medium in a separatory funnel. The chloroform fraction was removed after a separation time of 1 hr. Chloroform was evaporated at 40° C. using a Rotavapor R-3000 rotary evaporator (Büchi Laboratories, Flawil, Switzerland) and the remaining organic material was re-suspended in 6 mL of filtered nanopure water and evaporated to dryness using a Speed-Vac evaporator system (Savant Instruments, Inc., Hicksville, N.Y.) or lyophilized. These samples were then resuspended in culture medium or purified water. The final product is referred to as Chloroform extracted Spent Medium (CSM). Except where indicated, CSM was used in experiments at a final chloroform extracted organic carbon concentration 125 fold greater than found in spent medium.

Example 4—HPLC Fractionation of CSM

CSM was fractionated by High Performance Liquid Chromatography (HPLC) (Varian Prostar model 320, Varian Inc., Palo Alto, Calif.) using a C18 Microsorb-mv reverse phase column (Varian Inc.) dimensions 250×4.6 mm. The column was loaded with 100 µL of CSM and eluted in an acetonitrile/water gradient (2-75%) with a flow rate of 1 mL×min$^{-1}$ for 29 minutes. Samples were collected every minute, starting at 2 minutes. HPLC fractions were pooled and concentrated in a Speed Vac concentrator (Savant Instruments, Inc., Hicksville, N.Y.) and resuspended in 0.5 mL of modified EPRI medium or purified water. The active HPLC fraction was found to elute from the column in 70% acetonitrile/30% water. The active fraction of each HPLC separation was determined by microtiter plate dispersion bioassay.

Example 5—Microtiter Plate Dispersion Bioassay

Microtiter plate dispersion bioassays were used to test various preparations for their ability to exogenously induce biofilm dispersion. Biofilms were grown on the inside surface of microtiter plate wells using a semi-batch culture method in which the medium within each well was replaced periodically to reduce the accumulation of native dispersion inducing factors. Biofilms grown in this manner were treated with dispersion inducer or sterile medium to release cells into the bulk liquid and evaluate dispersed cell number by measuring optical density. Briefly, sterile polystyrene 96 well plates were etched with acetone for 10 seconds to create a rough surface for the attachment of microbial cells. After drying for 24 hours, plates were inoculated with 150 µL/well of overnight culture containing the test organism, previously diluted 1:20 in growth medium and incubated at 30° C. with shaking at 200 rpm. Medium in the wells was replaced every 24 hours for 5 days and every 12 hours on day 6 and day 7. Medium was then replaced after 7 hours. Dispersion induction was tested by adding 150 µL growth medium containing dispersion inducer for 1 hr at 30° C. or sterile medium as a control. Medium containing dispersed cells was then transferred by pipet to a non-etched microtiter plate and the optical density ($OD_{570}$) was determined (ELx808 Absorbance Microplate Reader; BioTek Instruments, Inc., Winooski, Vt.). Treatments consisted of spent medium, CSM, cis-2-decenoic acid, trans-decenoic acid, decanoic acid and DSF at various concentrations. Ethanol (10%) was used as a carrier for fatty acid inducer samples and was determined to have no influence on dispersion. Results from use of this method are meaningful in making comparisons of different treatments and to determine whether dispersion activity is statistically significant. Note: Microtiter plate dispersion bioassays were not suitable for determining absolute magnitude of an induced dispersion response because in a semi-batch system, control and test samples are susceptible to natural dispersion against which the activity of exogenous induction is measured. All efficiency studies were performed using biofilm tube reactor or flow-cell continuous culture systems and were based on both total cell counts and viable cell counts.

Example 6—Dispersion Bioassays in Biofilm Tube Reactors

*P. aeruginosa* PAO1 biofilm cultures were grown in tube reactors as described previously by Sauer et al. (K. Sauer, et al., *J. Bacteriol.* 184:1140 (2002), which is hereby incorporated by reference in its entirety). A continuous once-through tube reactor system was configured using 8 silicone reactor tubes (81.5 cm length×14 mm ID), connected to an 8-roller head peristaltic pump and medium reservoir, via additional silicone tubing. Medium was pumped through the tubing to a closed effluent medium reservoir. The assembled system was sterilized by autoclaving prior to inoculation. The silicone tubes were inoculated by syringe injection through a septum 1 cm upstream from each reactor tube, with 2 mL of overnight cultures of *P. aeruginosa* (containing approximately $1 \times 10^8$ CFU $mL^{-1}$). Bacterial cells were allowed to attach (static incubation) to the tubing for 1 hour, after which the flow was started at an elution rate of 10.8 mL $hr^{-1}$. Treatments were carried out following 96 hours of *P. aeruginosa* PAO1 biofilm cultures. The treatments were performed under continuous and static conditions.

Under continuous treatment (FIG. 17A) the influent medium was changed from fresh medium in the test lines to spent medium amended with 2% glucose, adjusted to neutrality and aerated overnight prior to addition. Control lines were switched to new lines containing fresh modified EPRI medium. Samples were collected for one minute intervals starting at time=0 min, and assayed for optical density. Spent medium was added at time=30 min. Samples were collected in test tubes on ice and were subsequently homogenized for 30 sec at 5000 rpm with a Tissue Tearor Model 985370 (Biospec Products, Inc.) to ensure separation of cells. Cell density was determined by optical density at 600 nm with an Ultrospec 3000 spectrophotometer (Amersham Pharmacia Biotech, Inc.).

Under conditions of static treatment, dispersion inducer was added by syringe injection through the inoculation port, 2 cm upstream from the beginning of the tube reactor, displacing the reactor volume with medium containing inducer. Spent medium was added directly. CSM or synthetic dispersion inducer (eg: cis-2-decenoic acid) was prepared in modified EPRI and added. After one hour of exposure under non-flowing conditions, an 81.5 cm length of each silicone tube reactor was cut out, the liquid fraction (containing released biofilm cells) was collected in test tubes on ice and the biofilm fraction was collected by rolling the tube on the lab bench with a metal rod to extrude the cells remaining in the lumen of the tube (K. Sauer, et al., *J. Bacteriol.* 184:1140 (2002), which is hereby incorporated by reference in its entirety). Samples were collected on ice, and homogenized as above. Cells numbers were determined by spread plate method on Standard Plate Count agar medium (Difco, Detroit, Mich.) or by optical density at $OD_{600}$ adjusted to cell number by calibration to a standard curve for cell number as determined microscopically by total cell count. Dispersion efficacy was calculated using either optical density or viability measurements:

$$\text{Dispersion Efficacy} = \frac{\text{Cells from Bulk Liquid} \times 100}{\text{Cells from Bulk Liquid} + \text{Cells from Biofilm}}$$

Example 7—Microscopic Analysis

A continuous-culture once-through flow cell was configured to observe the growth and development of biofilms attached to a glass substratum. The flow cell was constructed of aluminum containing a chamber 1.0 mm by 1.4 cm by 4.0 cm capped with a glass cover slip. Sterile modified EPRI medium was pumped from a 10-liter vessel through silicone tubing to the flow cell using a Masterflex 8-roller-head peristaltic pump at a flow rate of 0.13 mL $min^{-1}$. Flow through the chamber was laminar, with a Reynolds number of 0.17, having a fluid residence time of 4.3 min. Medium leaving the flow cell was discharged to an effluent reservoir via silicone tubing. The entire system was closed to the outside environment but maintained in equilibrium with atmospheric pressure by a 0.2-µm-pore-size gas-permeable filter fitted to each vessel. Log-phase *P. aeruginosa* (approximately $10^8$ CFU $mL^{-1}$) were inoculated as a 3.0 mL slug dose through a septum 4 cm upstream from the flow cell under flowing conditions. Cells attached to the inner surface of the glass cover slip were viewed by transmitted light or epi-UV illumination using an Olympus BX60 microscope and a 100× magnification A100PL objective lens or a 50× magnification ULWD MSPlan long working distance Olympus objective lens. All images were captured using a Magnafire cooled three-chip charge-coupled device (CCD) camera (Optronics Inc., Galena, Calif.) and stored as separate digital files for subsequent retrieval and analysis *P. aeruginosa* were grown in the flow cell for up to 12 days. Previous work by applicant has shown *P. aeruginosa* to develop steady-state biofilms following a continuous culture period of 7 to 9 days. Steady state is defined by no change in effluent cell counts (CFU) resulting from detached biofilm cells; in steady state, growth of the biofilm is balanced by the loss of cells through dispersion or detachment. Individual cell clusters were examined during the course of each experiment and assigned grid coordinates, which were reexamined periodically during the course of the experiments. Size measurements were taken of random cell clusters by locating the cluster nearest to a randomly selected microscope stage coordinate. Each cell cluster was measured to determine its height by focusing from the substratum through to the apex of the cluster, and its width by measurement at the base of the cell cluster using a stage micrometer. Cell clusters were defined as cells embedded within an exopolysaccharide matrix attached to the substratum and lacking motility; void areas within cell clusters were determined by the observation of free-swimming bacteria within a space inside a cell cluster.

Example 8—Inhibition of Biofilm Development

A flow cell was used to culture bacteria on the surface of a glass substratum (described above). Biofilms of *P. aeruginosa* were grown at room temperature over a period of 99 hours in the presence and absence of CSM (diluted 1:125 to match the concentration of the chloroform extracted organic material found in spent medium) in modified EPRI medium. During the course of the experiment, the total cell coverage of the bacteria on the surface and average biofilm thickness were determined by counting 20 microscope fields using a 50×ULWD MSPlan objective lens for each time point. Using the image analysis software, ImagePro Plus, the total area of cells per $cm^2$ was determined at 72 hours and 99 hours. Thickness was determined by measuring the average maximum height of 20 random cell clusters at 72 hours and 99 hours of growth. Control samples were grown and tested in the presence of modified EPRI medium with no added CSM. Results from these experiments showed that surface area coverage of the growing biofilm was significantly reduced when biofilms were grown in the presence of CSM compared to biofilms grown in EPRI medium alone. The addition of CSM also caused a significant reduction in the average biofilm cell cluster thickness after 99 hours growth, compared to samples not treated with CSM (FIG. 18).

Example 9—Spectral Analysis of *P. aeruginosa* CSM and cis-2-decenoic Acid

All CSM samples prepared in purified water were lyophilized and resuspended in appropriate carriers for each spectroscopic analysis. CSM controls in all experiments consisted of CSM HPLC products that did not induce dispersion as determined by microtiter plate dispersion bioassay, and carrier solution not containing CSM.

Example 10—Mass Spectroscopy

Samples were resuspended in carrier solution (50% water, 50% methanol and 0.01% formic acid). Mass spectroscopy was performed using a high-performance, hybrid quadrupole time-of-flight mass spectrometer—QSTAR® XL Hybrid LC/MS/MS System (Applied Bio systems, Foster City, Calif., USA)—in positive ion mode, at room temperature, with an IonSpray source for API 150EX™, API 3000™ and QSTAR® Systems (Applied Biosystems). Data were analyzed using Analyst QS version 1.1.

Example 11—Nuclear Magnetic Resonance (NMR)

Samples of CSM and cis-2-decenoic acid were resuspended in 1 mL of deuterated acetonitrile and inserted into a thin walled NMR sample tube (VWR). Analyzes was performed in a 300 MHz Proton NMR-Bruker AC 300 (Bruker Daltonics Inc., Vilarica, Mass., USA). Spectra were accumulated for 24 hours.

Example 12—Gas Chromatography-Mass Spectroscopy (GC-MS)

Samples of CSM and concentrations of cis-2-decenoic acid from 0.01 $mg \times mL^{-1}$-10 $mg \times mL^{-1}$ were resuspended in 2 mL of acetonitrile. A 3 step-sequential hexane extraction was performed to remove soluble organic sample material. Hexane was evaporated to dryness in a water bath (55-70° C.). Puridine (250 µL) was subsequently added to solubilize samples for injection into GC. Spectra were obtained with a Shimadzu QP5050A GC-MS system, using helium as a carrier as and a Restek (Columbia, Md.) XTI-5 GC column (30 m, 0.25 mm i.d., 0.25 µm film thickness) with a 1 $mL \times min^{-1}$ flow rate. All analyses incorporated splitless injection and electron impact ionization. The interface temperature between the GC and the MS was maintained at 310° C. Data were analyzed using the program Lab Solutions, GCMS solution version 1.2.

Example 13—Infrared Spectroscopy (IR)

Samples of CSM and cis-2-decenoic acid were weighed before and after lyophilization to determine the amount of KBr to add to each sample. KBr was added at 10 times the sample mass and mixed using a mortar and pestle. The resulting powder was formed into a pellet using a Carver 4350 Manual Pellet Press (Carver Inc., Wabash, Ind., USA). Pressure was applied at 10 Tons for 10 min. IR spectra were obtained using a Bruker Equinox 55 FT-IR spectrometer at room temperature in the range of 3500 $cm^{-1}$ to 400 $cm^{-1}$ at a resolution of 1 $cm^{-1}$. The final spectra represent the mean of 128 scans. Each sample was measured in triplicate.

Example 14—Biofilm Bacteria are Resistant to Antibiotics

Figure 1B:
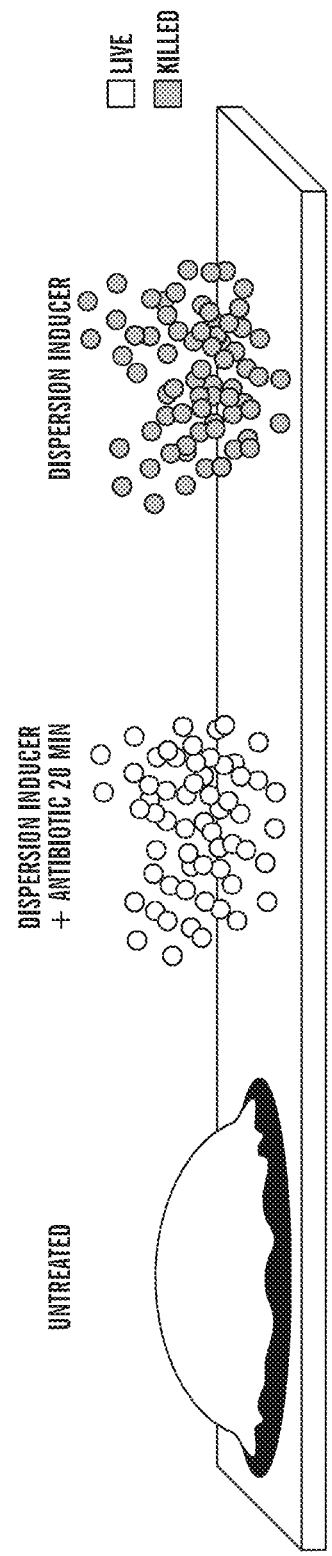

FIG. 1A illustrates schematically how biofilm bacteria are resistant to the addition of antibiotics, with similar resistance shown for biocides and other antimicrobial treatments. FIG. 1B illustrates that if a dispersion inducer is added in addition to antibiotic, the dispersed bacteria lose their resistance and become susceptible to the antibiotic.

Example 15—Effect of Dispersion Inducing Compounds

FIG. 2 shows an actual biofilm sample treated with the dispersion inducing compound according to the present invention, derived from cultures of *Pseudomonas aeruginosa*. In this experiment, a once-through flow-cell was used to culture *P. aeruginosa* over a period of six days prior to testing with added CSM.

The flow cell was constructed of anodized aluminum, containing a chamber 1.0 mm by 1.4 cm by 4.0 cm capped with a glass cover slip. Sterile EPRI medium was pumped from a 2-liter vessel through silicone tubing to the flow cell using a Masterflex 8-roller-head peristaltic pump at a flow rate of 0.13 ml $min^{-1}$. Flow through the chamber was laminar, with a Reynolds number of 0.17, having a fluid residence time of 4.3 min. Medium leaving the flow cell was discharged to an effluent reservoir via silicone tubing. The entire system was closed to the outside environment but maintained in equilibrium with atmospheric pressure by a 0.2-μm-pore-size gas-permeable filter fitted to each vessel. Log-phase *P. aeruginosa* (approximately $10^8$ CFU/ml) were inoculated as a 3.0-ml slug dose through a septum 4 cm upstream from the flow cell under flowing conditions. Cells attached to the inner surface of the glass cover slip were viewed by transmitted light using an Olympus BX60 microscope and a 50× magnification ULWD MSPlan long working distance Olympus objective lens. All images were captured using a Magnafire cooled three-chip charge-coupled device (CCD) camera (Optronics Inc., Galena, Calif.) and stored as separate digital files for subsequent retrieval and analysis. Following development of a mature biofilm within the flow-cell, medium-flow was stopped and 3 mL of filtered CSM in sterile EPRI medium was added to the flow-cell. Transmitted light images of a single location within the flow-cell were taken before and during treatment with CSM. FIG. 2 shows images taken from such an experiment 1 min prior to addition of CSM, 5 min after addition of CSM, and 30 min after addition of CSM. Control samples were also run in the same manner as the test samples with the exception that CSM was not included with the 6 mL of added EPRI medium. Results from the control samples showed no change in biofilm cell numbers or biofilm architecture, with no dispersion evident.

Example 16—Biofilm Bacteria Undergo a Phenotypic Switch

Figure 3A:
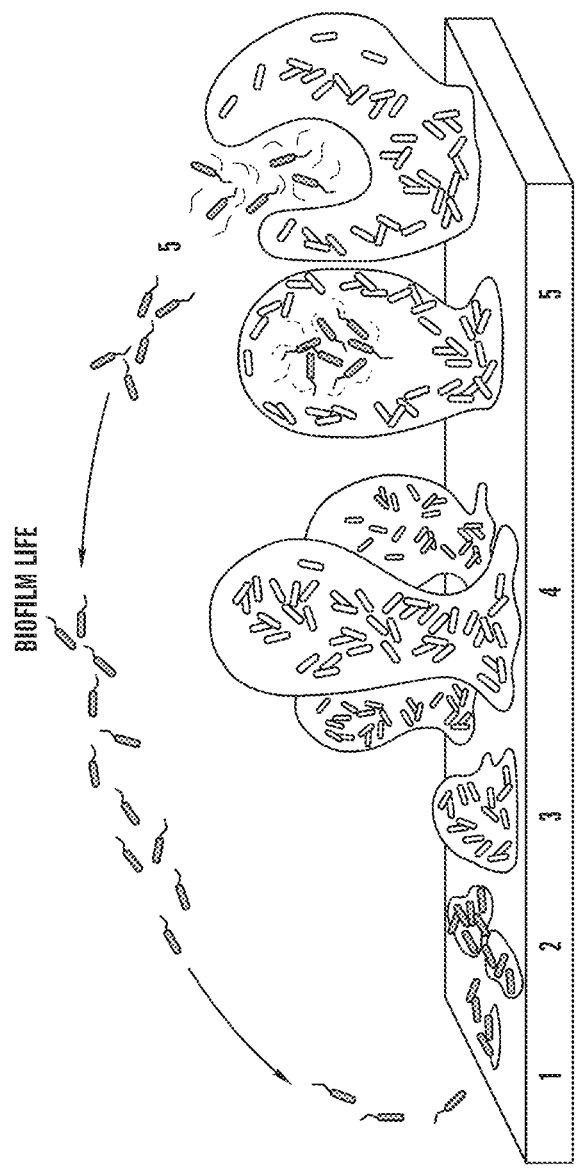
FIG. 3A is a schematic representation of the life cycle of a biofilm. 1, Planktonic bacteria are transported (actively and passively) to the substratum. 2, Cell surface molecules interact with the substratum resulting in reversible surface attachment. 3, Phenotypic changes in the bacterial cell result in cell surface modifications and the production of extracellular polymeric substances, which irreversibly cement the cells to the surface. 4, Physiological changes continue with alterations in metabolism, cell-cell signaling and morphology as biofilm maturation occurs. 5, Cells release degradative enzymes to digest matrix polymer material and alter surface appendages as biofilm detachment occurs. The series of photomicrographs at the bottom of FIG. 3B, show, in order, phase contrast photomicrographs of the five stages of biofilm development by P. aeruginosa grown in continuous culture in a flow-cell and imaged by microscopy. (Sauer et al., "Pseudomonas aeruginosa Displays Multiple Phenotypes During Development as a Biofilm," J. Bacteriol. 184:1140-1154 (2002), which is hereby incorporated by reference in its entirety).
Figure 3B:
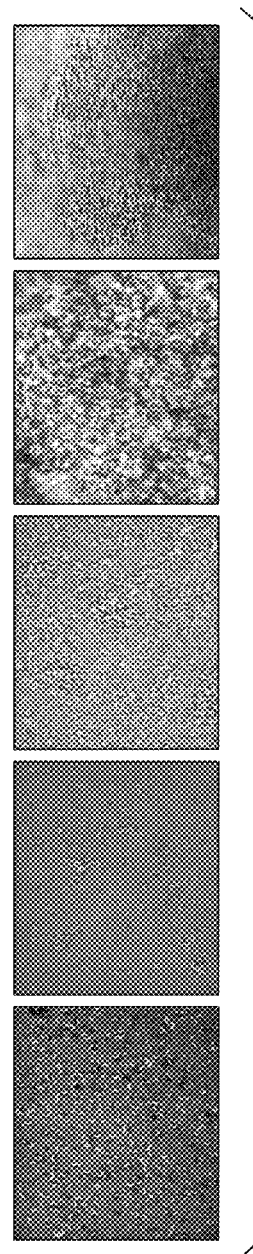

During the course of normal biofilm development, biofilm bacteria undergo a phenotypic switch at the end of maturation II stage (FIG. 3) in which their physiology changes from a predominantly biofilm form to a predominantly planktonic form. Microscopic observations of biofilms during the dispersion phase demonstrated that bacteria within cell clusters become motile (maturation stage *P. aeruginosa* are non-motile), while the bacteria around the edges of the clusters remain fixed. The region of the cell cluster within which bacteria can swim/twitch grows in volume from a (usually) central location and eventually a breach is made in the cluster wall. The bacteria are able to swim through this breach and enter the bulk liquid phase leaving behind a void within the cell cluster.

Continued study of the dispersion response has revealed that cell clusters transition through episodes of growth and dispersion; the same cell cluster often enduring many such cycles. Multiple dispersion and regrowth events generally lead to the development of cell clusters with patterns analogous to growth rings which can indicate the number of times that dispersion has occurred. Often cell clusters will detach from the substratum completely during a dispersion event (Stoodley et al., "Growth and Detachment of Cell Clusters from Mature Mixed-species Biofilms," *Appl. Environ. Microbiol.* 67:5608-5613 (2001), which is hereby incorporated by reference in its entirety). This effect is thought to be due to weakening of attachment structures at the base of the cell cluster allowing fluid sheer to detach the cluster.

Example 17—Cell Detachment after Medium Stagnation

Figure 4A:
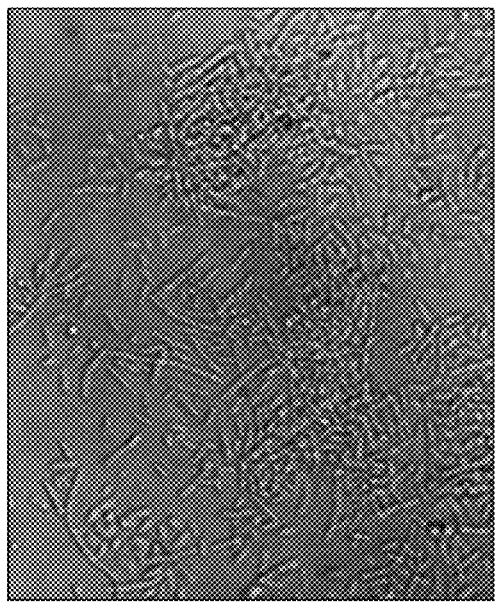
FIGS. 4A-B are phase contrast photomicrographs of biofilm 20 dispersion induced by cessation of flow.
Figure 4B:
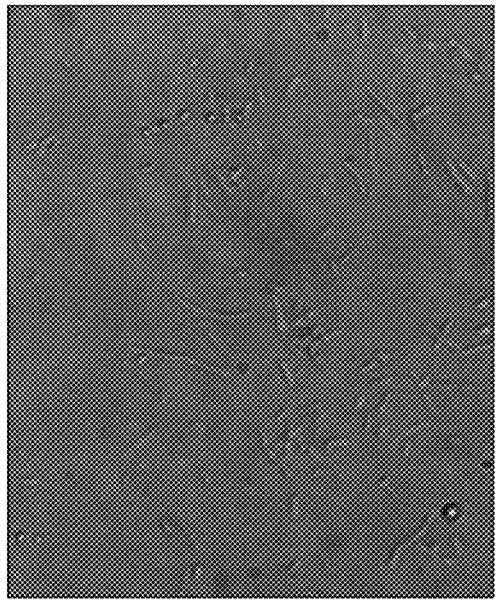
Figure 5:
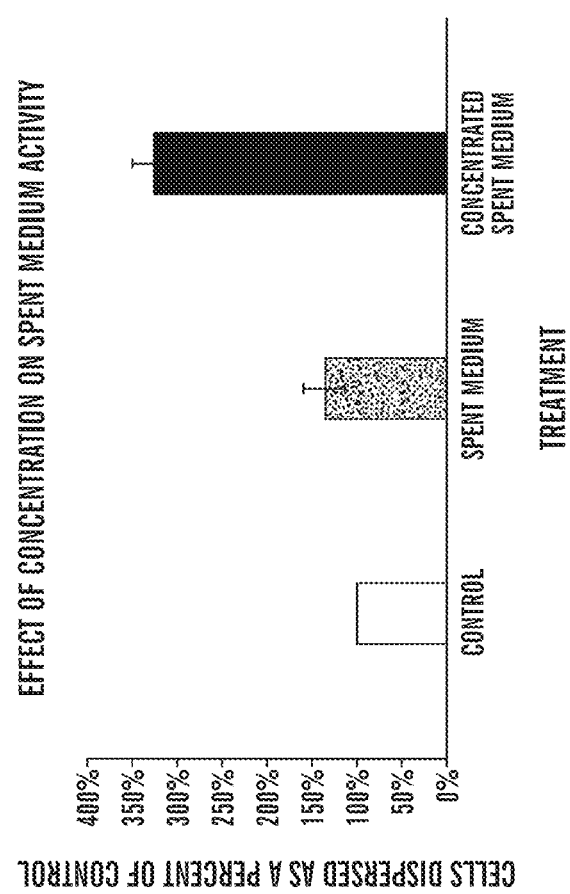
FIG. 5 is a graph showing the effect of chloroform extraction on spent medium dispersion activity. Biofilms were cultured for six days in continuous culture in EPRI medium in biofilm tube reactors (Sauer et al., "Pseudomonas aeruginosa Displays Multiple Phenotypes During Development as a Biofilm," J. Bacteria 184:1140-1154 (2002), which is hereby incorporated by reference in its entirety) and treated with spent medium (control) and chloroform extracted spent medium (CSM). Cell dispersion was determined as the optical density of culture effluent collected at the end of culture tubes. The error bar represents standard deviation for three replicate experiments.

FIG. 4 depicts a time series of phase contrast photomicrographs showing the detachment of cells after medium stagnation of 72 hours. Flow-cell were inoculated with *P. aeruginosa* PAO1 and cultured for a period of three days, according to the method described in Example 3, above. The choice of three days for culture of these biofilms was based upon the observation that under continuous flow, cell clusters within a biofilm of *P. aeruginosa* were observed to undergo spontaneous dispersion events following 9 days of incubation. After 72 days of growth under continuous flow, medium flow was stopped and images of the cell clusters were recorded every two hours for a period of 96 hours. After 72 hours of medium stagnation, the cell clusters within the flow-cell were observed to dis-aggregate, with cells entering the bulk liquid medium as planktonic bacteria (FIG. 4). These experiments demonstrated that cessation of flow induced dispersion of biofilms. response. In these experiments, dispersion occurred not simply within the cell clusters, but throughout all clusters in the biofilm. Only those cells which were directly attached to the substratum were not observed to swim into the bulk liquid, as illustrated in FIG. 4.

Example 18—Development of Chloroform Extraction Method

Various growth and extraction procedures were tested to develop a reliable method of extracting the active fraction of spent culture medium having dispersion inducing activity. Chloroform was chosen as the extraction solvent of choice due to its compatibility with HPLC fractionation procedures, because it resulted in a narrow range of extractable organic compounds (as determined by mass spectrometry) and because it could recover bioactive amounts of the dispersion inducing agent. The method currently used for chloroform extraction of spent medium follows: Bacterial cultures of *P. aeruginosa* PAO1 were grown in 4 liters of EPRI medium (containing: sodium lactate 0.05 g/l, sodium succinate 0.05 g/l, ammonium nitrate 50.381 g/l, $KH_2PO_4$ 0.19 g/l, $K_2HPO_4$ 0.63 g/l, Hutner Salts metals solution 1 ml, and glucose, 2.0 g/l) in a batch culture vessel for six days at room temperature with continuous stirring. Following growth, bacteria were removed from the culture medium by centrifugation at 10,000×g for 20 min, followed by filtration of spent medium through a 0.22 μm pore size filter. In batches, 250 ml of filtered spent medium were mixed with 80 ml of chloroform in a reparatory funnel. The chloroform fraction was removed after a separation time of 10 min. The chloroform samples were then evaporated to dryness at 70° C. using a rotavapor R-3000 (Büchi Laboratories, Flawil, Switzerland) and re-suspended in 6 mL of filtered nanopure water or EPRI medium. The final product, resulting from the chloroform extraction procedure is referred to here as concentrated spent medium or CSM. FIG. 15 shows the results of comparing the effect of CSM and Spent Medium on continuous culture biofilms grown in biofilm tube reactors. CSM and Spent medium were prepared as described previously from cultures of *P. aeruginosa* PAO1 grown at 22° C. for 9 days in EPRI medium supplemented with 2.0 gram per Liter of glucose. Biofilms of *P. aeruginosa* PAO1 were cultured for six days at 22° C. in biofilm tube reactors consisting of 32 cm silicone dioxide Masterflex size 14 tubing. At the end of six days, 6 mL of CSM, Spent Medium or Sterile EPRI medium, each supplemented with 2.0 gram per Liter glucose, was added to the tubes. The effluent from the tubes was collected and pooled for each treatment over a period of 20 minutes. Pooled sampled were assayed for optical density at 570 nm to determine relative cell numbers dispersed from each treatment. Each experiment was performed with five replicates. Results from these experiments demonstrated that chloroform extracted spent culture medium, CSM showed a greater activity in dispersing biofilms of *P. aeruginosa* compared to spent medium.

Figure 6A:
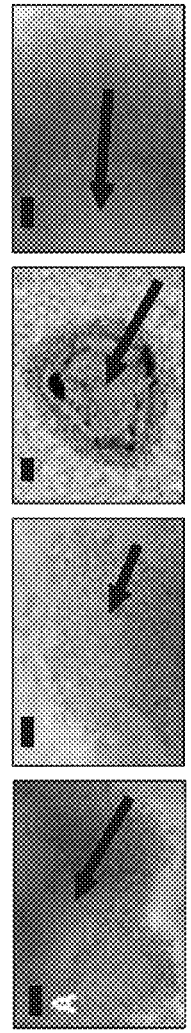
FIG. 6A shows microcolonies of P. aeruginosa biofilms grown in continuous culture demonstrating native dispersion response. During the dispersion stage of biofilm development, bacteria become motile within cell clusters and exit to the bulk liquid through a breach in the microcolony wall. Each photomicrograph shows a microcolony whose interior has been voided in this manner. The arrow indicates the location of a void. Images taken at 1000× magnification; bar represents 10 μm.
Figure 6B:
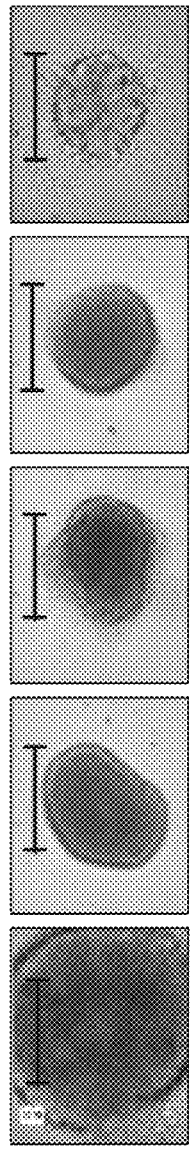
FIG. 6B is a transmitted light image.
Figure 6C:
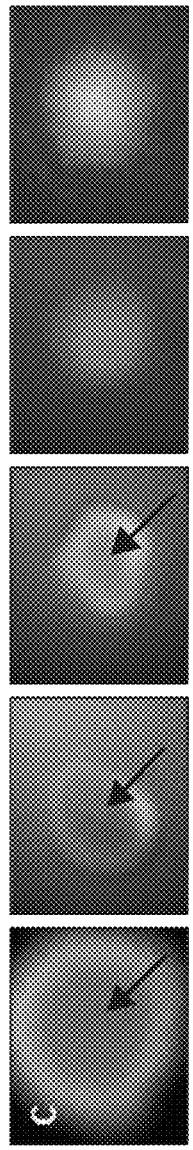
FIG. 6C is a fluorescent image showing the size dependence of dispersion response. Biofilm microcolonies growing in continuous culture having dimensions of greater than 40 μm diameter×10 μm thickness show dispersion (left 3). Microcolonies below this minimum dimension remain "solid" (right 2 photomicrographs). Fluorescence indicates presence of cells (lacZ reporter on chromosome). All images are the same relative size at 500× magnification; bars represent 40 μm. Arrows indicate void areas within microcolony.

Applicant observed that *P. aeruginosa* PAO1 will disperse from a continuous culture biofilm grown on a glass substratum in a flow-cell reactor after medium flow had been stopped for several hours. This observation has led to the hypothesis that biofilm dispersion may result from the accumulation of an extracellular messenger which acts as an inducer of biofilm disaggregation. This hypothesis is supported by observations that biofilms of *P. aeruginosa* will not form in batch culture flasks, but will form on the walls of a chemostat, indicating that accumulation of a signal for dispersion may prevent biofilm development. Furthermore, when grown in continuous culture, microcolonies of *P. aeruginosa* will form hollow voids at their center when they attain a minimum diameter of 40 microns and thickness of 10 microns (FIG. 6). The microcolony size within which these voids form, however, is dependent on the fluid flow rate. When flow in a biofilm reactor was increased, the diameter and thickness at which microcolony void formation occurred also increased, indicating a relationship between dispersion induction and transport. These observations hinted that an extracellular substance produced by *P. aeruginosa* was responsible for inducing biofilm dispersion.

Figure 7B:
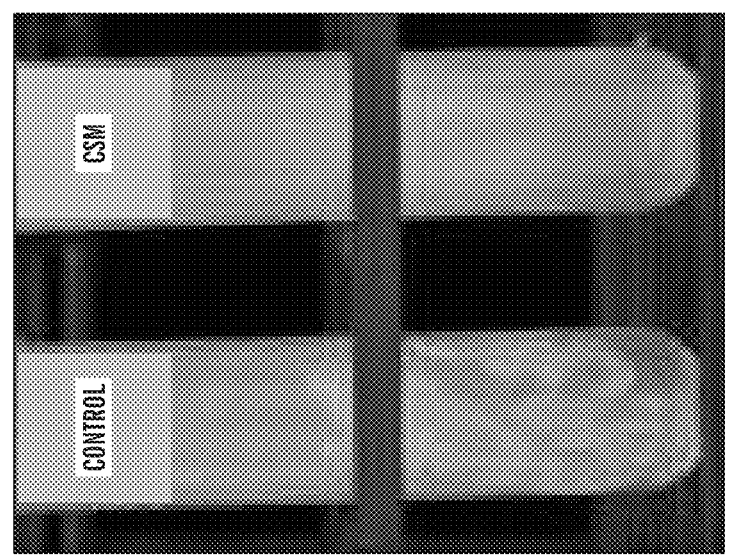
Figure 7A:
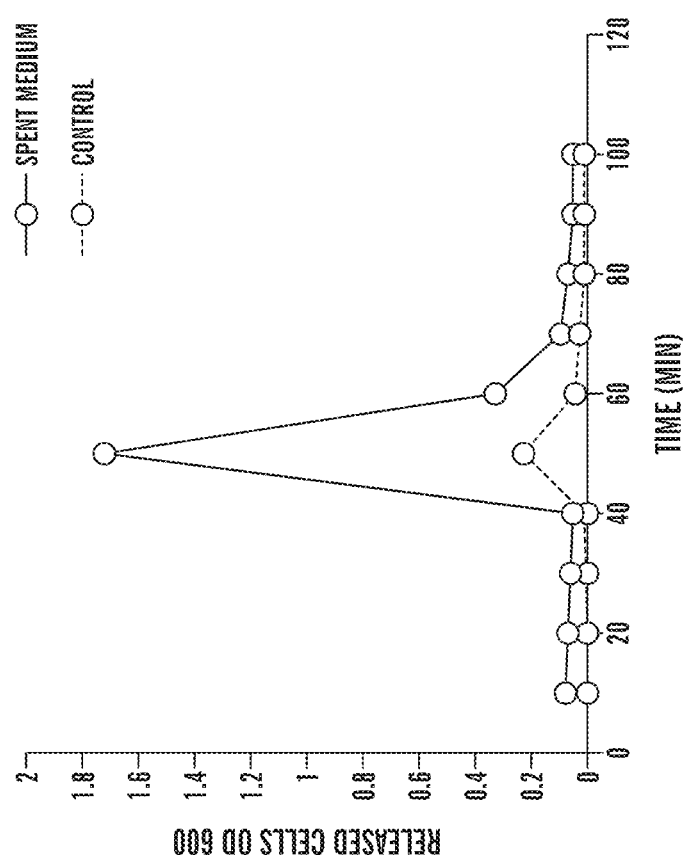

If *P. aeruginosa* produces an extracellular dispersion-inducing compound, applicant postulated that the addition of cell-free spent culture medium to mature *P. aeruginosa* biofilms should cause the release of cells into the bulk liquid medium. These bacteria should be detectable as an increase in the number of cells recovered in the reactor effluent. FIG. 7A illustrates results from a representative experiment in which biofilms were treated for 70 minutes under continuous flow with cell-free spent medium in which *P. aeruginosa* had been grown in suspension for 24 hours; fresh medium was added to control biofilms. Prior to addition, spent medium was aerated, supplemented with glucose and its pH adjusted to neutrality, to ensure that starvation, oxygen depletion or a change in pH was not responsible for the release of bacteria. A large spike in the effluent cell number was detectable compared to control lines within 20 minutes of the addition of the spent medium, indicating the release of biofilm bacteria into the effluent of cultures treated with spent medium. A small spike of released cells was also detectable in control samples, likely representing a response to the physical or mechanical effects associated with switching lines to a fresh medium reservoir.

To purify the active dispersion inducing fraction of spent medium, cell-fee stationary-phase batch cultures of *P. aeruginosa* were extracted using chloroform, followed by rotory evaporation of the chloroform and re-suspension of the organic fraction in fresh medium or buffer solution (resulting in a 125-fold increase in the chloroform-soluble organic fraction). This preparation is referred to as CSM. To test the dispersion-inducing activity of CSM, *P. aeruginosa* biofilms were grown in continuous culture in silicone tubing and exposed the biofilms for one hour to medium amended with CSM. The extruded contents of the tube reactors showed a largely intact biofilm in the control line treated with fresh medium (FIG. 7B), while the contents of the tubes treated with CSM showed the biofilm to have completely disaggregated (FIG. 7C). Studies of 4-day old biofilms grown in continuous culture in silicone tubing revealed that treatment with CSM-containing medium for one hr was effective in releasing an average 87.4% (±1.4%) of biofilm cells as determined by colony forming units released into the effluent. Spent medium was shown to have an average dispersion efficacy of 32.4% (±5.5%).

Microscopy was used to evaluate the effect of CSM on biofilm microcolonies grown for six days in continuous culture on the glass substratum of a flow-cell mounted to a microscope (K. Sauer et al., *J. Bacteriol.* 184:1140 (2002), which is hereby incorporated by reference in its entirety). Prior to the addition of CSM, a well-developed microcolony was observed to contain cells that were stationary and showed no sign of motility (FIG. 7D). Following 7 minutes of contact with CSM-containing medium, cells within the microcolony began to twitch and display active motility (FIG. 7E). After 30 minutes, the microcolony had become completely disaggregated and cells were observed to swim freely through the medium (FIG. 7F). When compared to natural dispersion, exogenously induced dispersion was observed to progress from the outside of the microcolony towards the interior and, instead of creating a central void, resulted in complete disaggregation of the microcolony.

Figure 8A:
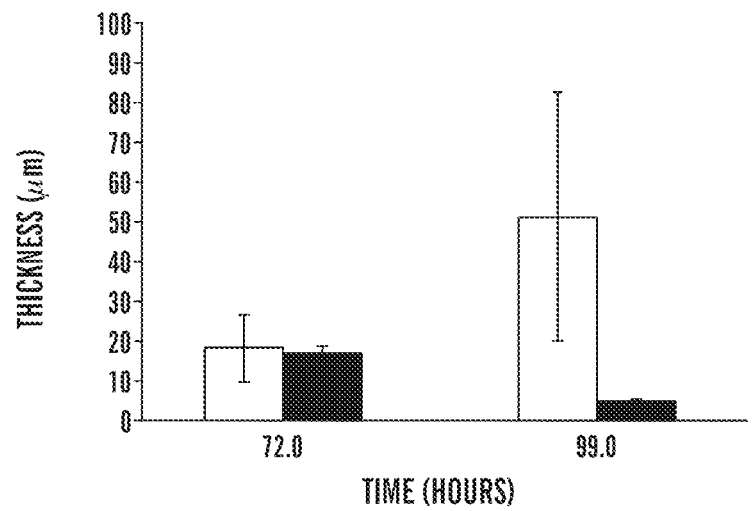
FIGS. 8A-B show biofilm development in the continuous presence of CSM diluted in modified EPRI to concentration of Spent medium. Average thickness (FIG. 8A) and surface area of biofilms grown in the presence of CSM (FIG. 8B) are significantly less than for untreated biofilms. Grey bars, biofilms treated with CSM. Black bars, biofilms grown in the absence of dispersion inducer. Error bars represent one standard deviation for 20 randomly selected microcolonies
Figure 8B:
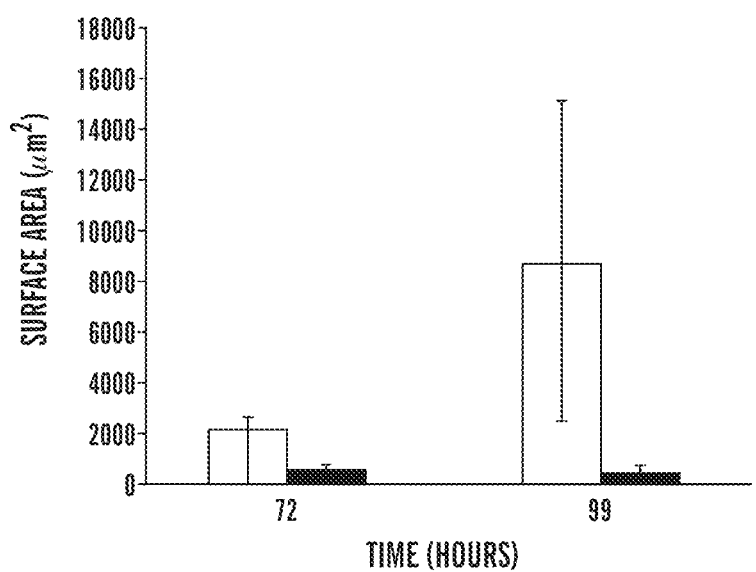

When added continuously to flow cells, CSM adjusted to the concentration of spent medium, showed a significant inhibition of biofilm development over a period of 99 hr, demonstrating a reduction in both biofilm average thickness and surface area coverage (FIG. 8). Exogenous dispersion induction of pre-formed biofilms by CSM was measurable at all time points from day 1 (beginning of biofilm microcolony formation) through day 6, after which natural dispersion began to occur. Activity of CSM was shown to persist up to 6 months with no significant reduction when stored under refrigeration. Extraction of spent medium by ethyl acetate (to recover acyl-homoserine lactones) did not result in a preparation with dispersion activity.

Figure 9:
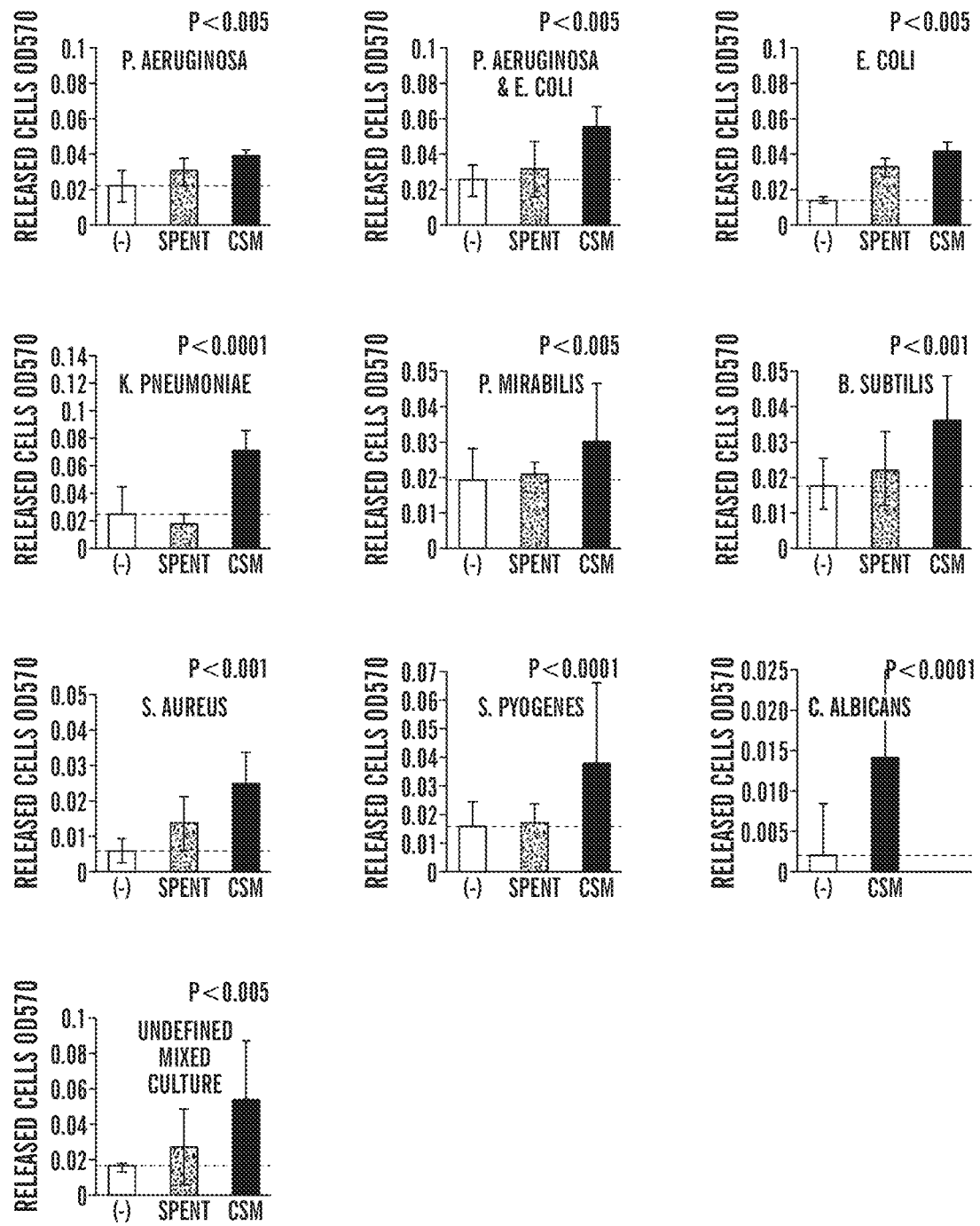
FIG. 9 shows dispersion of different bacterial biofilms by P. aeruginosa CSM using microtiter plate dispersion bioassay. Y-axis indicates number of cells released into the bulk liquid of 16 replicate wells in 3 replicate experiments, following treatment for 1 hr with CSM or carrier control (−), containing sterile medium. Hatched line indicates level of dispersion in carrier control samples. All differences between CSM samples and controls are statistically significant at indicated P-value as determined by Student's T-test.

Having demonstrated dispersion induction against mature and developing biofilms formed by *P. aeruginosa*, the ability of CSM to induce dispersion in biofilm cultures of *E. coli*, *E. coli* mixed with *P. aeruginosa*, an undefined mixed bacterial biofilm derived from airborne contaminants, and against biofilms formed by *Klebsiella pneumoniae*, *Proteus mirabilis*, *Streptococcus pyogenes*, *Bacillus subtilis*, *Staphylococcus aureus*, and *Candida albicans* was next tested. CSM was shown to stimulate significant dispersion compared to controls in all samples tested. Results from these experiments are summarized in FIG. 9. The ability of *P. aeruginosa* dispersion inducer to activate dispersion in different species of bacteria and in yeast indicates that it possesses cross-phylum and cross-kingdom activity.

Figure 10A:
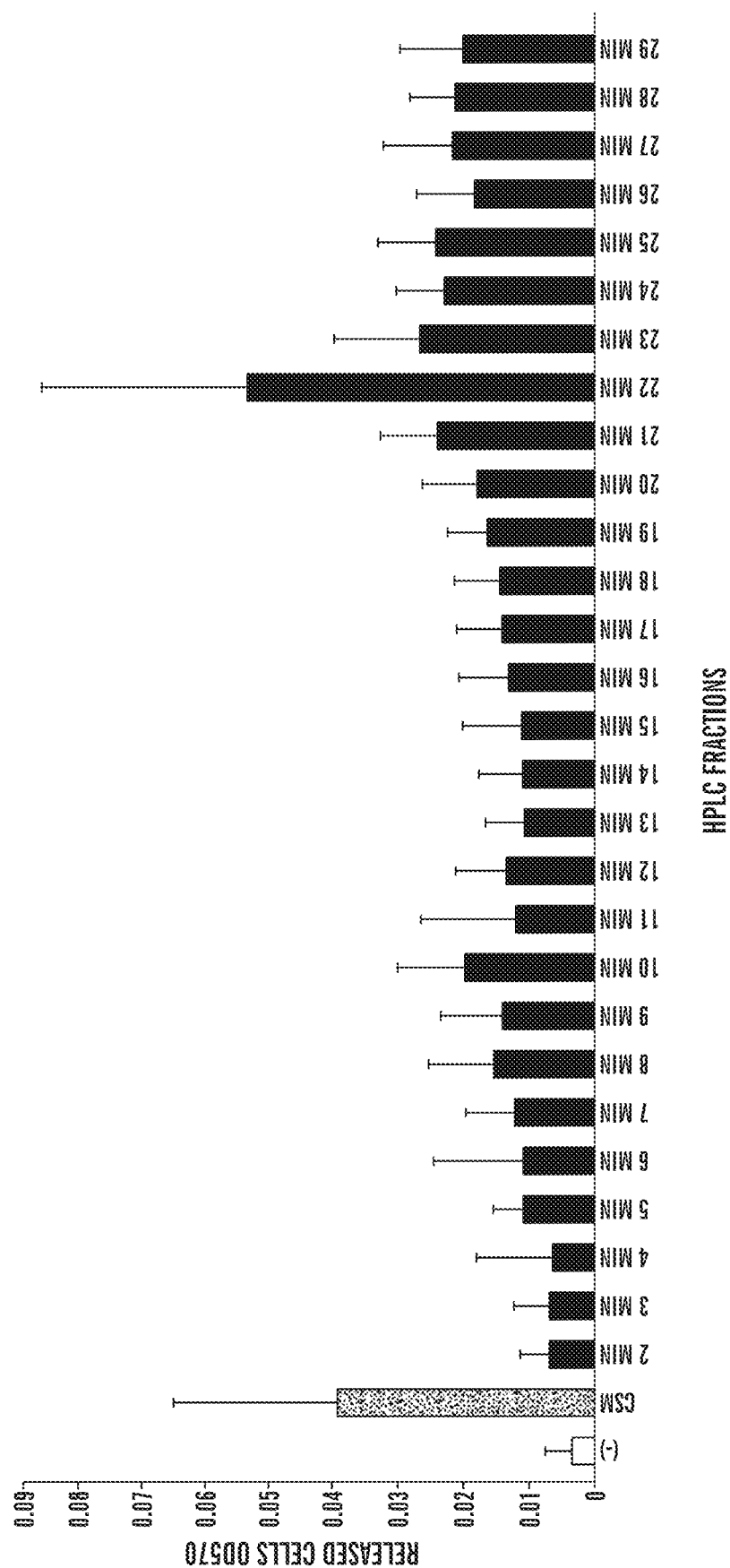

Having established the role of CSM as an inducer of biofilm dispersion, the active molecule or molecules present in CSM was identified. This began by assaying the dispersion activity of multiple fractions of CSM separated by Isocratic gradient in acetonitrile and water using C-18 reverse phase high performance liquid chromatography (HPLC). Eluted HPLC fractions (collected at one minute intervals) were desiccated in a Speedvac to remove residual acetonitrile and re-suspended in purified water and tested by microtiter plate dispersion bioassay to determine dispersion activity. FIG. 10A shows the results of CSM fractionation biofilm dispersion assays. The results indicated that the HPLC fraction of CSM showing the highest activity eluted at 22 min, an acetonitrile/water ratio of 70%/30%.

Mass spectrometry of the active HPLC CSM fraction showed a consistent molecular peak with low ionization activity at 171 M/Z (mw=170). This peak was present in all samples showing dispersion activity and missing from all samples lacking dispersion activity. This peak was also shown to be missing from all carrier liquids and solvents used in preparing CSM (including fresh culture medium). Mass spectroscopy-product ion analysis of the 170 mw peak, solubility analysis, $H^1$- and $C^{13}$ nuclear magnetic resonance (NMR) spectroscopy and infra-red (IR) spectroscopy have demonstrated that the 170 mw molecule was a mono-unsaturated $C_{10}$-fatty acid, with a double bond located at the number 2 carbon; 2-decenoic acid.

Figure 12A:
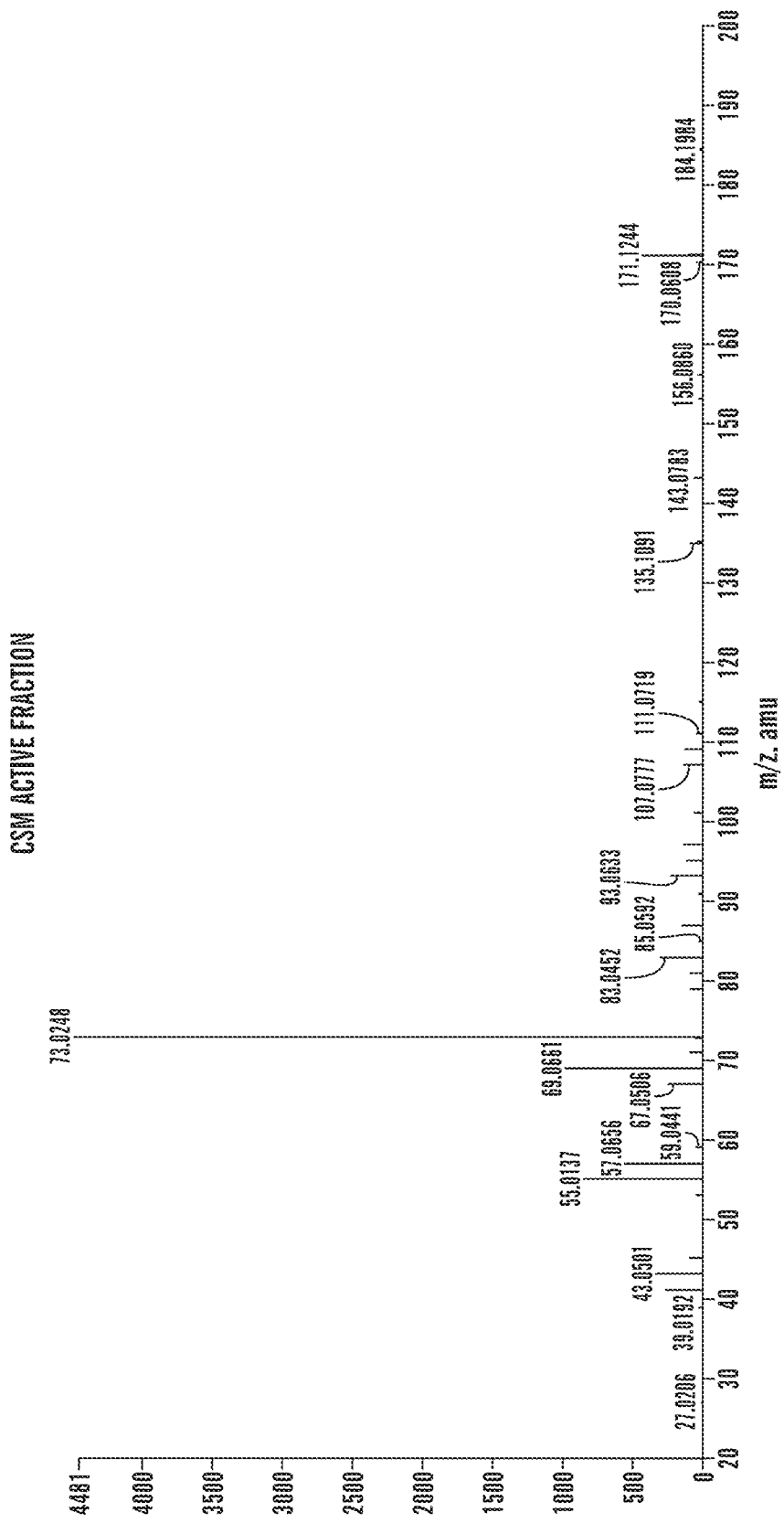
FIGS. 12A-C show the spectral analysis of P. aeruginosa CSM and cis-2-decenoic acid.
Figure 12A:
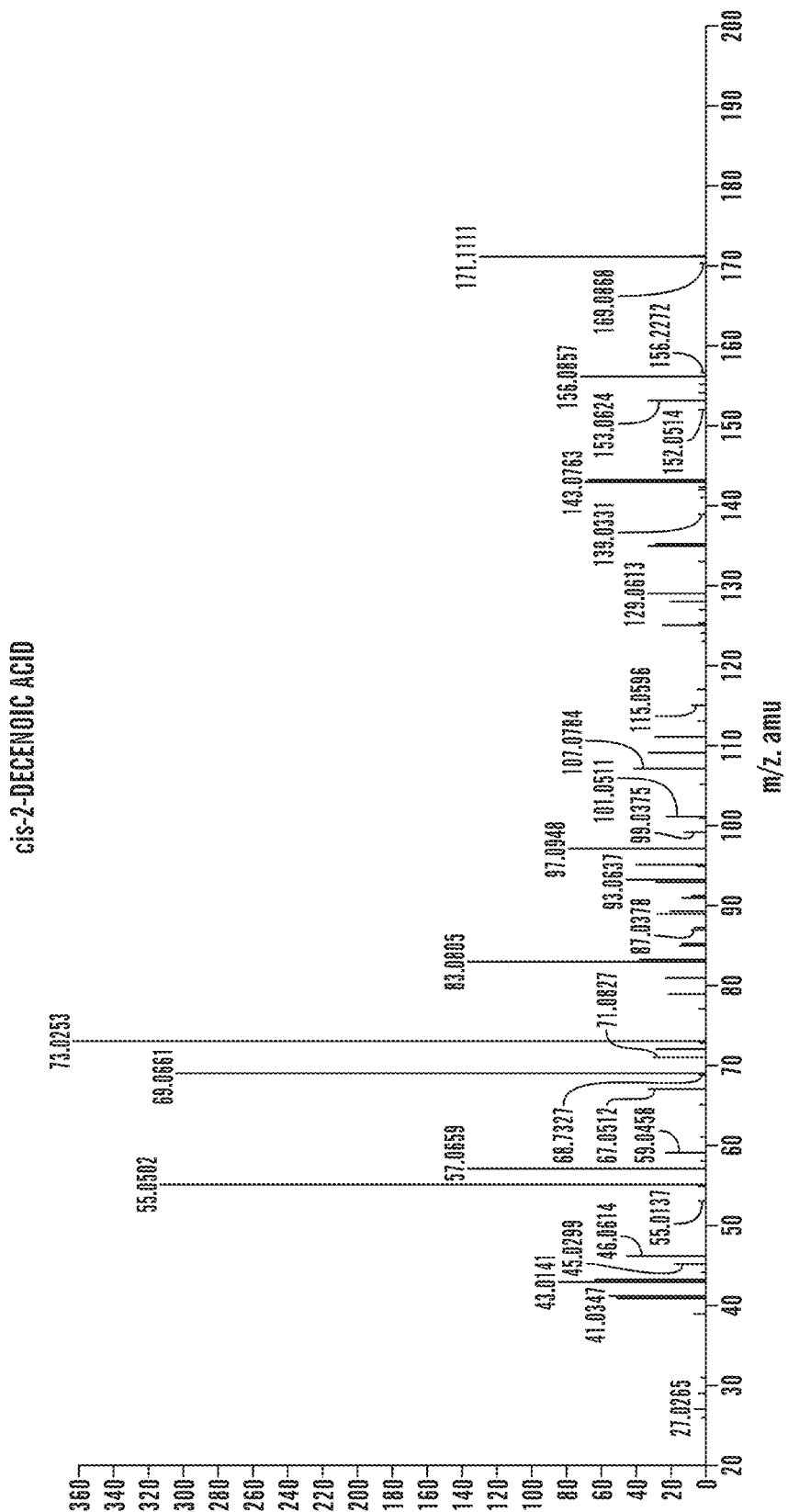
Figure 12B:
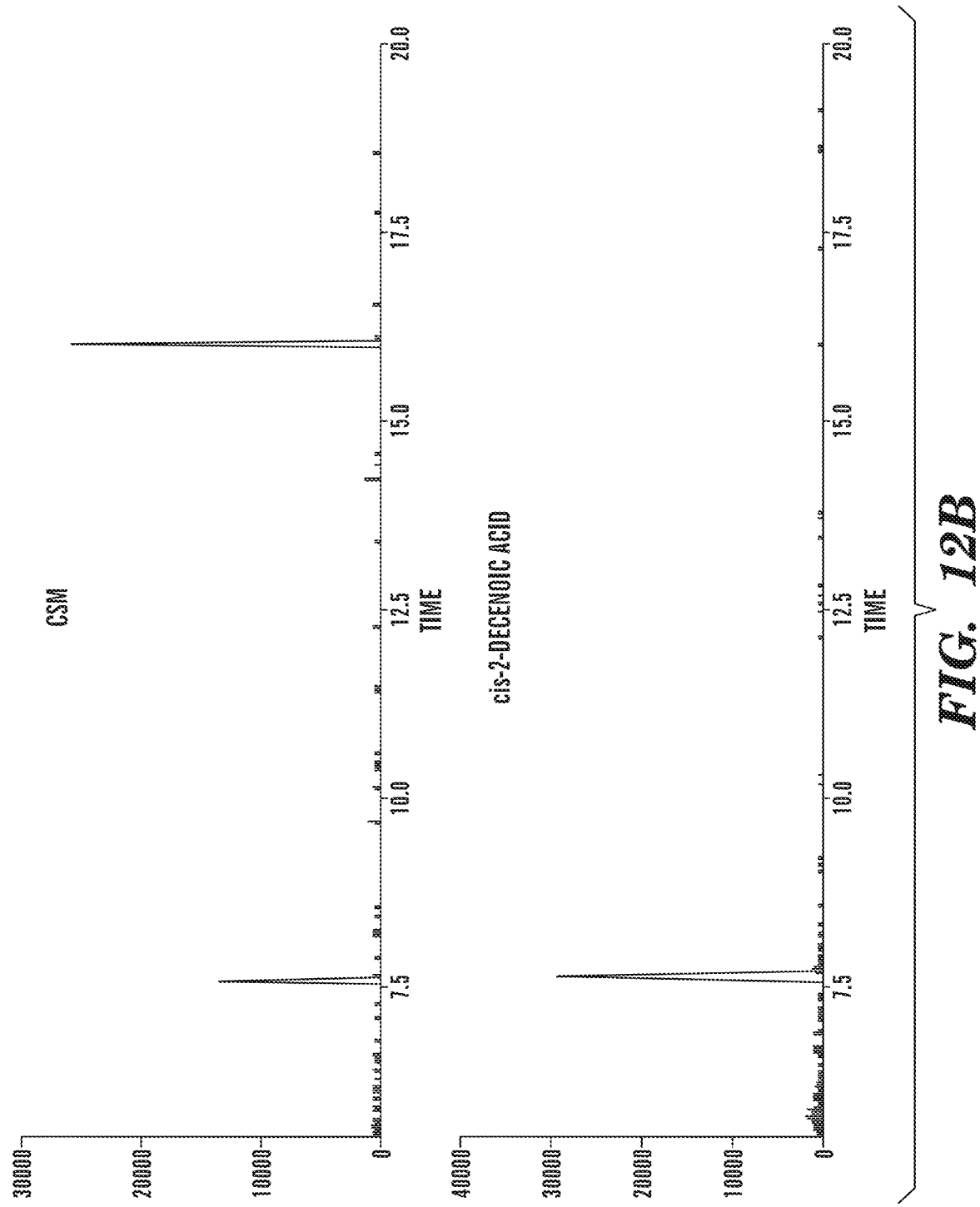
Figure 12C:
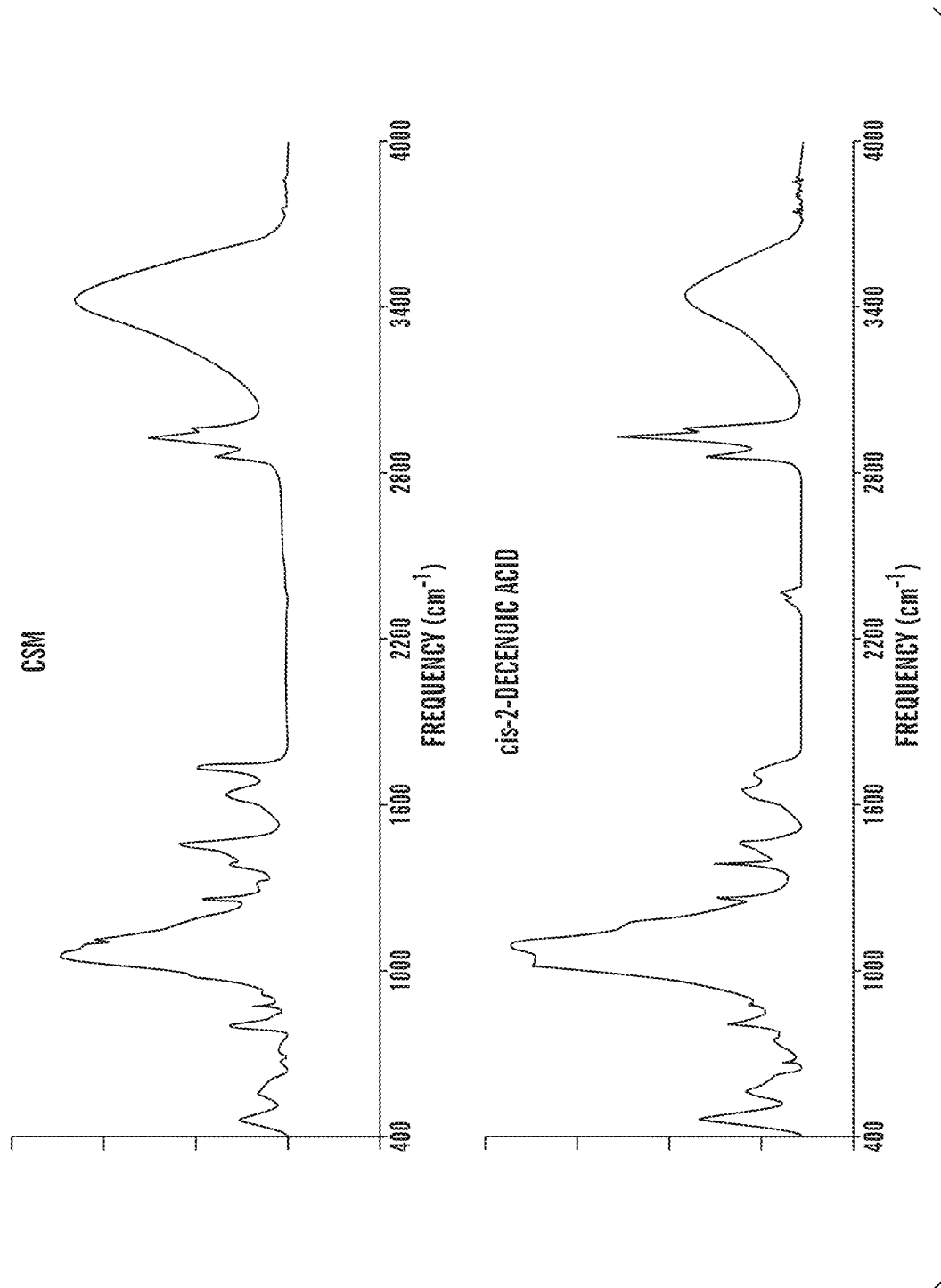

In order to confirm that the 170-mw molecule (M/Z=171) from the 22-minute CSM HPLC fraction was identical to 2-decenoic acid, the original molecule was fragmented in the mass spec to generate product ion peaks. The product ions from the active CSM fraction and 2-decenoic acid were analyzed by quadrapole ms/ms to evaluate cleavage differences between these two molecules. FIG. 12A, shows that the 171 M/Z CSM sample had identity with 2-decenoic acid. When analyzed by GC-MS, unfractionated CSM displayed a single major peak with a retention time of 7.6 min identical to that of 2-decenoic acid FIG. 12B. Infrared spectroscopy confirmed that the cis isomer of 2-decenoic acid was the organic compound isolated from CSM, FIG. 12C.

Figure 11:
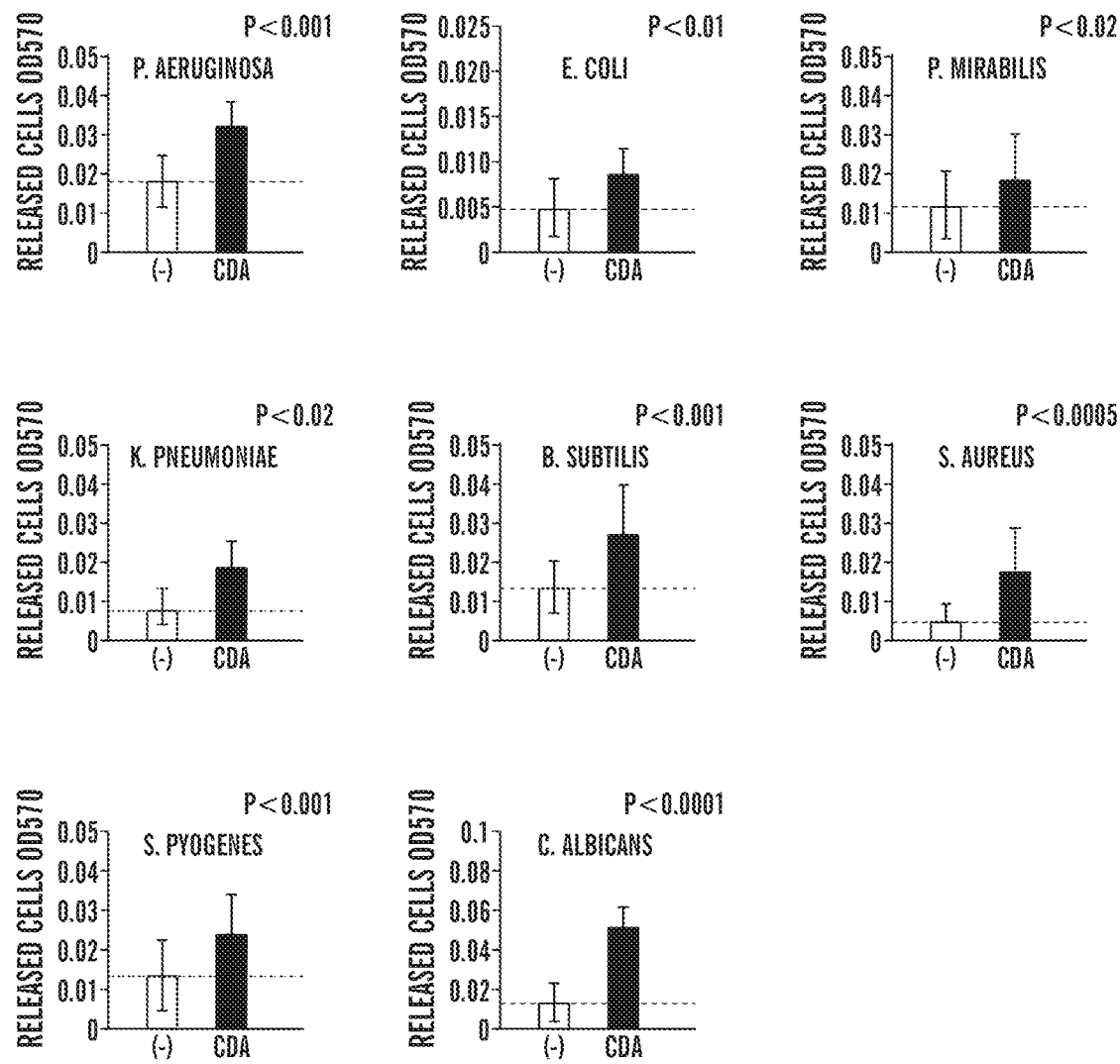
FIG. 11 shows dispersion of different bacterial biofilms by cis-2-decenoic acid using microtiter plate dispersion bioassay. Y-axis indicates number of cells released into the bulk liquid of 16 replicate wells in 3 replicate experiments, following treatment for 1 hr. with 0.01 μM cis-2-decenoic acid (CDA), or carrier control (−), containing medium+10% ethanol. Hatched line indicates level of dispersion in carrier control samples. All differences between cis-2-decenoic acid treated samples and controls are statistically significant at indicated P-value as determined by Student's T-test.
Figure 13:
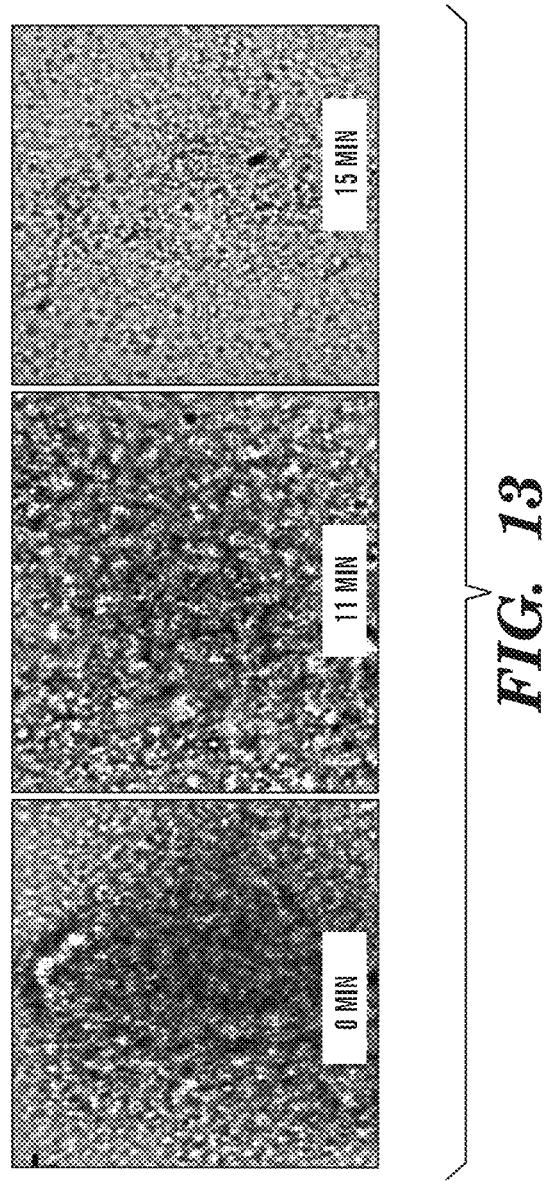
FIG. 13 shows the addition of 10 μM cis-2-decenoic acid (cis-DA) to mature biofilm grown in continuous culture in a microscope-mounted flow cell. Microcolony disaggregation is shown to begin at 11 min. Complete microcolony disaggregation is shown within 15 min exposure. Control biofilms treated with carrier fluid were not affected by treatment up to 1 hr.

Following this identification, mono-unsaturated fatty acid molecules of various molecular weights were synthesized and tested these for dispersion activity. DSF, which was shown to disrupt cell flocs of *X. campestris* was shown not to promote dispersion of *P. aeruginosa*. The compounds having the highest activity were two isomers of 2-decenoic acid. The trans isomer (trans-2-decenoic acid) was shown by microtiter plate dispersion bioassay to have activity only at millimolar concentrations, typically not low enough to qualify as a cell-cell signaling molecule. FIG. 10B shows the dispersion activity of increasing concentrations of cis-2-decenoic acid against biofilm cultures of *P. aeruginosa* grown in microtiter plates. These results demonstrated that the cis isomer (cis-2-decenoic acid) was active over a concentration range of 1.0 nanomolar to 10 millimolar, showing greater dispersion activity at 1.0 nanomolar than un-concentrated spent culture medium (i.e.: higher than the naturally occurring inducer). Microscopy revealed that the activity of cis-2-decenoic acid as a dispersion inducer was similar to CSM activity, completely disrupting a biofilm microcolony as shown in FIG. 13. The activity of cis-2-decenoic acid was also tested against *E. coli, S. pneumonia, P. mirabilis, S. pyogenes, B. subtilis, S. aureus*, and *C. albicans* biofilm cultures, resulting in similar results to those obtained for CSM (FIG. 11).

This study has shown that a small messenger fatty acid molecule, cis-2-decenoic acid, is produced by *P. aeruginosa* in batch and biofilm culture. This molecule has been demonstrated to induce a dispersion response in biofilms formed by *P. aeruginosa* and a range of gram-negative and gram-positive bacteria and in yeast. The dispersion response is a mechanism to escape starvation conditions within a population, allowing fixed cells the opportunity to migrate to a more favorable environment and thin out the population that remains, allowing cells to obtain increased nutrients. When biofilm microcolonies are small, the inducer, which accumulates in the extracellular matrix is removed by diffusive and advective transport. This removal is not possible in batch systems. When cell clusters attain a dimension where the inducer is not adequately washed out from the interior (the rate of diffusion being exceeded by the rate of production), the inducer is able to attain a concentration necessary for activation of the dispersion response, releasing cells from the biofilm. The discovery of a cell-to-cell signaling molecule responsible for biofilm dispersion allows the exogenous induction of the transition of biofilm bacteria to a planktonic state. Use of this dispersion inducer is likely to result in enhanced treatment options in combating biofilm-related infections and in the control of microbial bio fouling.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A dentifrice composition comprising:
   cis-2-decenoic acid, wherein the concentration of cis-2-decenoic acid in the composition is 0.001 µM to 30 µM, said dentifrice composition being selected from the group consisting of breath spray, tooth powder, whitening strips, prophylaxis strips, breath strips, lozenges, and breath mints.

2. A dentifrice composition comprising:
   cis-2-decenoic acid, wherein the concentration of cis-2-decenoic acid in the composition is 0.001 µM to 30 µM and
   one or more additives selected from the group consisting of fluoride, desensitizing agents, anti-tartar agents, antibacterial agents, remineralization agents, whitening agents, and anti-caries agents.

3. A mouthwash composition comprising:
   cis-2-decenoic acid, wherein the concentration of cis-2-decenoic acid in the composition is 0.001 µM to 30 µM and
   one or more additives selected from the group consisting of fluoride, desensitizing agents, anti-tartar agents, antibacterial agents, remineralization agents, whitening agents, and anti-caries agents.

4. A toothpaste composition comprising:
   cis-2-decenoic acid, wherein the concentration of cis-2-decenoic acid in the composition is 0.001 µM to 30 µM;
   a fluoride or remineralization agent; and
   an orally-accepted vehicle.

5. A toothpaste composition comprising:
   cis-2-decenoic acid, wherein the concentration of cis-2-decenoic acid in the composition is 0.001 µM to 30 µM and
   a sulfate.

6. A toothpaste composition comprising:
   cis-2-decenoic acid, wherein the concentration of cis-2-decenoic acid in the composition is 0.001 µM to 30 µM and
   one or more agents selected from the group consisting of baking soda, enzymes, vitamins, herbs, calcium compounds, flavoring agents, desensitizing agents, antibacterial agents, and antiplaque agents.

* * * * *